US011207522B2

(12) United States Patent
Vaidyanathan

(10) Patent No.: US 11,207,522 B2
(45) Date of Patent: Dec. 28, 2021

(54) NOTIFICATION INDICATIVE OF A CHANGE IN EFFICACY OF THERAPY

(71) Applicant: Medtronic, Inc., Minneapolis, MN (US)

(72) Inventor: Janardan Vaidyanathan, Thane (IN)

(73) Assignee: Medtronic, Inc., Minneapolis, MN (US)

( * ) Notice: Subject to any disclaimer, the term of this patent is extended or adjusted under 35 U.S.C. 154(b) by 1339 days.

(21) Appl. No.: 13/750,624

(22) Filed: Jan. 25, 2013

(65) Prior Publication Data

US 2014/0213926 A1 Jul. 31, 2014

(51) Int. Cl.
*A61B 5/00* (2006.01)
*A61B 5/375* (2021.01)
*A61N 1/36* (2006.01)

(52) U.S. Cl.
CPC .......... *A61N 1/36135* (2013.01); *A61B 5/375* (2021.01); *A61N 1/36067* (2013.01); *A61N 1/36139* (2013.01)

(58) Field of Classification Search
None
See application file for complete search history.

(56) References Cited

U.S. PATENT DOCUMENTS

| 5,449,377 | A | * | 9/1995 | Adams | .................. | A61N 1/3956 607/7 |
| 5,683,422 | A | | 11/1997 | Rise | | |
| 5,833,709 | A | | 11/1998 | Rise et al. | | |
| 6,066,163 | A | | 5/2000 | John | | |
| 6,164,284 | A | | 12/2000 | Schulman et al. | | |
| 6,463,328 | B1 | | 10/2002 | John | | |
| 7,184,837 | B2 | | 2/2007 | Goetz | | |
| 7,209,787 | B2 | | 4/2007 | DiLorenzo | | |
| 7,239,926 | B2 | | 7/2007 | Goetz | | |
| 7,617,002 | B2 | | 11/2009 | Goetz | | |
| 7,706,889 | B2 | | 4/2010 | Gerber et al. | | |
| 7,715,920 | B2 | | 5/2010 | Rondoni et al. | | |

(Continued)

FOREIGN PATENT DOCUMENTS

WO 2010044989 A2 4/2010
WO 2011053543 A1 5/2011

OTHER PUBLICATIONS

Volkmann et al., "Basic Algorithms for the Programming of Deep Brain Stimulation in Parkinson's Disease," Movement Disorders, vol. 21, Suppl. 14, 2006, pp. S284-S289.

(Continued)

*Primary Examiner* — Etsub D Berhanu
(74) *Attorney, Agent, or Firm* — Shumaker & Sieffert, P.A.

(57) ABSTRACT

In some examples, a processor is configured determine whether efficacy of therapy delivered by a medical device to the patient may have changed and generate a notification based on the determination. For example, a processor may be configured to determine whether a bioelectrical brain signal indicative of activity of a brain of a patient includes a biomarker that indicates efficacy of therapy delivered by a medical device to the patient may have changed, and generate notification based on determining the bioelectrical brain signal includes the biomarker. In some examples, the processor modifies the therapy delivered to the patient prior to generating the notification.

35 Claims, 8 Drawing Sheets

(56) References Cited

U.S. PATENT DOCUMENTS

| | | | |
|---|---|---|---|
| 7,801,619 B2 | 9/2010 | Gerber et al. | |
| 7,983,757 B2 | 7/2011 | Miyazawa et al. | |
| 8,078,281 B2 | 12/2011 | Priori et al. | |
| 8,185,207 B2 | 5/2012 | Molnar et al. | |
| 8,190,251 B2 | 5/2012 | Molnar et al. | |
| 2002/0123693 A1* | 9/2002 | Lange | A61B 5/0478 600/544 |
| 2003/0013981 A1* | 1/2003 | Gevins | A61B 5/0484 600/544 |
| 2004/0133119 A1* | 7/2004 | Osorio | A61B 5/048 600/544 |
| 2006/0116737 A1 | 1/2006 | Libbus | |
| 2006/0094970 A1* | 5/2006 | Drew | A61B 5/0006 600/509 |
| 2006/0224222 A1 | 10/2006 | Bradley et al. | |
| 2007/0244407 A1* | 10/2007 | Osorio | A61B 5/4094 600/544 |
| 2007/0249954 A1* | 10/2007 | Virag | A61B 5/02405 600/544 |
| 2007/0287931 A1* | 12/2007 | Dilorenzo | A61B 5/0476 600/545 |
| 2008/0167571 A1* | 7/2008 | Gevins | A61B 5/0484 600/544 |
| 2008/0319511 A1* | 12/2008 | Pless | A61B 5/0031 607/59 |
| 2009/0083070 A1 | 3/2009 | Giftakis et al. | |
| 2009/0118786 A1 | 5/2009 | Meadows et al. | |
| 2010/0100153 A1 | 4/2010 | Carlson et al. | |
| 2011/0137371 A1 | 6/2011 | Giftakis et al. | |
| 2011/0144521 A1 | 6/2011 | Molnar et al. | |
| 2011/0144715 A1 | 6/2011 | Molnar et al. | |

OTHER PUBLICATIONS

Moro et al., "Subthalamic Nucleus Stimulation: Improvements in Outcome With Reprogramming," Archives of Neurology, 2006;63:1266-1272 (Sep. 2006).

Nager et al., "Beta-oscillations in the posterior hypothalamus are associated with spontaneous cluster headache attack," J Neurol (May 14, 2010), 257:1743-1744.

International Search Report and Written Opinion from counterpart International application No. PCT/US2013/036119, dated Aug. 19, 2013, 12 pp.

International Preliminary Report on Patentability from International Application No. PCT/US2013/036119, dated Jul. 28, 2015, 7 pp.

Communication Pursuant to Rules 161(1) and 162 EPC dated Sep. 22, 2015 from counterpart European Application No. 13722162.8, 2 pp.

Response to Communication pursuant to Rules 161(1) and 162 EPC dated Sep. 22, 2015, from counterpart European Application No. 13722162.8, filed Apr. 1, 2016, 7 pp.

Examination Report from counterpart European Application No. 13722162.8, dated May 8, 2017, 4 pp.

Response to Examination Report dated May 8, 2017, from counterpart European Application No. 13722162.8, filed Sep. 18, 2017, 7 p.

Extended Search Report from counterpart European Application No. 20195485.6, dated Dec. 11, 2020, 6 pp.

Decision to Grant from counterpart European Application No. 13722162.8, dated Dec. 10, 2020, 1 pp.

* cited by examiner

NOTIFICATION INDICATIVE OF A CHANGE IN EFFICACY OF THERAPY

TECHNICAL FIELD

The disclosure relates to therapy delivery by a medical device.

BACKGROUND

Implantable medical devices, such as electrical stimulators or therapeutic agent delivery devices, may be used in different therapeutic applications, such as deep brain stimulation (DBS), spinal cord stimulation (SCS), pelvic stimulation, gastric stimulation, peripheral nerve stimulation, functional electrical stimulation or delivery of pharmaceutical agent, insulin, pain relieving agent or anti-inflammatory agent to a target tissue site within a patient. A medical device may be configured to deliver therapy to a patient to treat a variety of symptoms or patient conditions such as chronic pain, tremor, Parkinson's disease, other types of movement disorders, seizure disorders (e.g., epilepsy), urinary or fecal incontinence, sexual dysfunction, obesity, mood disorders, gastroparesis or diabetes. In some therapy systems, an implantable electrical stimulator delivers electrical therapy to a target tissue site within a patient with the aid of one or more electrodes, which may be deployed by medical leads. In addition to or instead of electrical stimulation therapy, a medical device may deliver a therapeutic agent to a target tissue site within a patient with the aid of one or more fluid delivery elements, such as a catheter or a therapeutic agent eluting patch.

During a programming session, which may occur during implant of the medical device, during a trial session, or during an in-clinic or remote follow-up session after the medical device is implanted in the patient, a clinician may generate one or more therapy programs (also referred to as therapy parameter sets) that provide efficacious therapy to the patient, where each therapy program may define values for a set of therapy parameters. A medical device may deliver therapy to a patient according to one or more stored therapy parameter sets, which may also be referred to as therapy programs. In the case of electrical stimulation, the therapy parameters may define characteristics of the electrical stimulation waveform to be delivered. In examples in which electrical stimulation is delivered in the form of electrical pulses, for example, the parameters may include an electrode combination, an amplitude, which may be a current or voltage amplitude, a pulse width, and a pulse rate.

SUMMARY

The disclosure describes example systems, devices, and methods for determining that efficacy of one or more therapy parameter values with which therapy is delivered to a patient may have changed, such that evaluation of the one or more therapy parameter values may be desirable. In some examples, one or more processors are configured to determine, based on a sensed bioelectrical brain signal, whether efficacy of one or more therapy parameter values with which therapy is delivered to a patient may have changed. In some examples, the processor is configured to generate a notification (e.g., delivered to the patient, patient caretaker, or clinician) in response to determining that the bioelectrical brain signal indicates efficacy of one or more therapy parameter values with which therapy is delivered to a patient may have changed. The notification may, for example, indicate that evaluation of the one or more therapy parameter values may be desirable, e.g., to re-program the medical device.

In some examples, a processor is configured to modify at least one therapy parameter value of the one or more therapy parameter values in response to determining efficacy of the one or more therapy parameter values may have changed. The processor may be configured to undertake the therapy modification automatically or in response to user input. In response to determining the modification to the at least one therapy parameter value did not sufficiently improve the efficacy of the therapy delivered by the medical device, the processor may generate the notification.

In one example, the disclosure is directed to a method that comprises receiving, with one or more processors, information representative of a bioelectrical brain signal of a patient, determining, with the one or more processors, whether the bioelectrical brain signal includes a biomarker that indicates efficacy of therapy delivered by a medical device to the patient may have changed, and generating, with the one or more processors, a notification based on determining the bioelectrical brain signal includes the biomarker In another example, the disclosure is directed to a system that comprises a sensing module configured to sense a bioelectrical brain signal of a patient, and one or more processors configured to determine whether the bioelectrical brain signal includes a biomarker that indicates efficacy of therapy delivered by a medical device to the patient may have changed, and generate a notification based on determining the bioelectrical brain signal includes the biomarker.

In another example, the disclosure is directed to a system that comprises means for receiving information representative a bioelectrical brain signal of a patient, means for determining whether the bioelectrical brain signal includes a biomarker that indicates efficacy of therapy delivered by a medical device to the patient may have changed, and means for generating a notification based on determining the bioelectrical brain signal includes the biomarker.

In another aspect, the disclosure is directed to a computer-readable medium containing instructions that, when executed by one or more processors, cause the one or more processors to receive information representative of a bioelectrical brain signal of a patient, determine whether the bioelectrical brain signal includes a biomarker that indicates efficacy of therapy delivered by a medical device to the patient may have changed, and generate a notification based on determining the bioelectrical brain signal includes the biomarker.

In another aspect, the disclosure is directed to a computer-readable storage medium, which may be an article of manufacture. The computer-readable storage medium includes computer-readable instructions for execution by one or more processors. The instructions cause one or more processors to perform any part of the techniques described herein. The instructions may be, for example, software instructions, such as those used to define a software or computer program. The software or computer program may be, for example, modified or otherwise updated base on a specific patient's requirements. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. In some examples, the computer-readable storage medium is non-transitory.

The details of one or more examples are set forth in the accompanying drawings and the description below. Other features, objects, and advantages will be apparent from the description and drawings, and from the claims.

DETAILED DESCRIPTION

The disclosure describes example systems, devices, and methods for determining when evaluation of one or more therapy parameter values with which therapy is delivered to a patient may be desirable. The therapy parameter values with which a medical device (implantable or external) generates and delivers therapy to a patient may be defined as part of a set of therapy parameter values, which may also be referred to herein as a "therapy program" in some examples. In some aspects, the disclosure describes example systems, devices, and methods for generating a notification that indicates that evaluation of the one or more therapy parameter values with which the medical device is currently generating and delivering therapy to a patient may be desirable, e.g., to re-program the medical device, such as by selecting one or more different or additional therapy programs for delivering therapy to the patient. The notification may be delivered to the patient, a patient caretaker, a clinician, or another suitable recipient. The notification may be delivered to the patient, a patient caretaker, a clinician, or another suitable recipient using any suitable technique. For example, the notification may be one or more of a visual notification, an audible notification, or a somatosensory notification provided via a medical device, a patient programmer, a clinician programmer, a remote device (e.g., transmitted to a remote clinician device), or another device, which may or may not be co-located with the patient.

Figure 1:
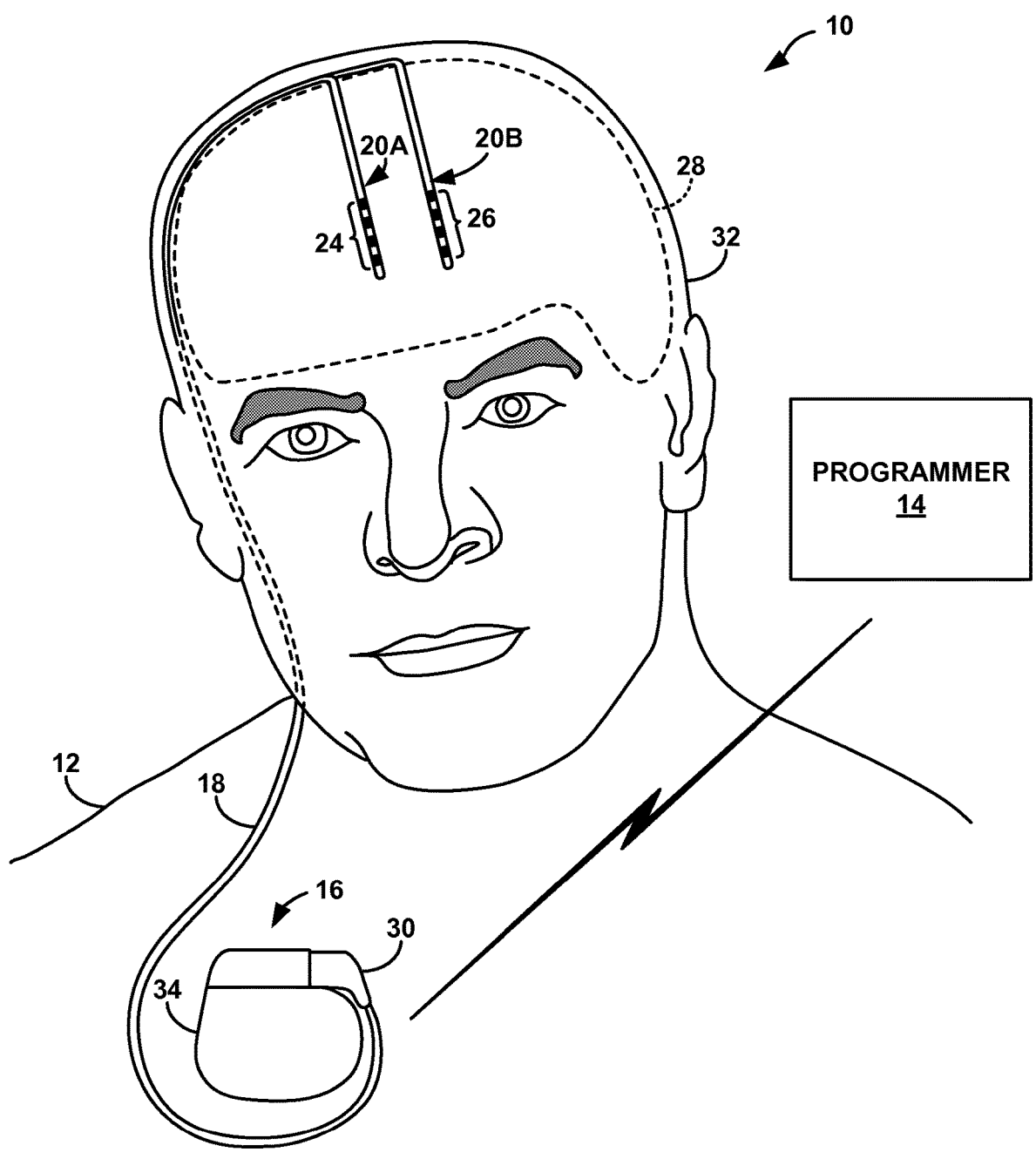
FIG. 1 is a conceptual diagram illustrating an example deep brain stimulation (DBS) system for delivery of an example electrical stimulation therapy to a tissue site within a brain of a patient.

FIG. 1 is a conceptual diagram illustrating an example therapy system 10 that is configured to deliver therapy to patient 12 to manage a disorder of patient 12. In some examples, therapy system 10 may deliver therapy to patient 12 to manage a movement disorder or a neurodegenerative impairment of patient 12. Patient 12 ordinarily will be a human patient. In some cases, however, therapy system 10 may be applied to other mammalian or non-mammalian non-human patients. A movement disorder may be characterized by one or more symptoms, such as, but not limited to, impaired muscle control, motion impairment or other movement problems, such as rigidity, bradykinesia, rhythmic hyperkinesia, nonrhythmic hyperkinesia, dystonia, tremor, and akinesia. In some cases, the movement disorder may be a symptom of Parkinson's disease or Huntington's disease. However, the movement disorder may be attributable to other patient conditions.

Although movement disorders are primarily referred to throughout the remainder of the application, in other examples, therapy system 10 may be configured to deliver therapy to manage other patient conditions, such as, but not limited to, seizure disorders (e.g., epilepsy), psychiatric disorders, behavior disorders, mood disorders, memory disorders, mentation disorders, Alzheimer's disease, or other neurological or psychiatric impairments, in addition to or instead of a movement disorder. Examples of psychiatric disorders include major depressive disorder (MDD), bipolar disorder, anxiety disorders, post traumatic stress disorder, dysthymic disorder, and obsessive compulsive disorder (OCD). Treatment of other patient disorders via delivery of therapy to brain 28 or another suitable target therapy delivery site in patient 12 is also contemplated.

In the example shown in FIG. 1, therapy system 10 includes medical device programmer 14, implantable medical device (IMD) 16, lead extension 18, and one or more leads 20A and 20B (collectively "leads 20") with respective sets of electrodes 24, 26. IMD 16 includes a therapy module that includes a stimulation generator that is configured to generate and deliver electrical stimulation therapy to one or more regions of brain 28 of patient 12 via a subset of electrodes 24, 26 of leads 20A and 20B, respectively. In the example shown in FIG. 1, therapy system 10 may be referred to as a deep brain stimulation (DBS) system because IMD 16 provides electrical stimulation therapy directly to tissue within brain 28, e.g., a tissue site under the dura mater of brain 28 or one or more branches or nodes, or a confluence of fiber tracks. In other examples, leads 20 may be positioned to deliver therapy to a surface of brain 28 (e.g., the cortical surface of brain 28). In some examples, IMD 16 may provide cortical stimulation therapy to patient 12, e.g., by delivering electrical stimulation to one or more tissue sites in the cortex of brain 28. In some examples, IMD 16 may provide vagal nerve stimulation (VNS) therapy to patient 12 by delivering electrical stimulation to one or more vagal nerve tissue sites.

Although electrical stimulation therapy is primarily referred to throughout the remainder of the application, in other examples, therapy system 10 may be configured to deliver other types of therapy in addition to or instead of electrical stimulation therapy, such as, e.g., drug delivery therapy.

In the example shown in FIG. 1, IMD 16 may be implanted within a subcutaneous pocket above the clavicle of patient 12. In other examples, IMD 16 may be implanted within other regions of patient 12, such as a subcutaneous pocket in the abdomen or buttocks of patient 12 or proximate the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16 within a chest cavity of patient 12, along the neck of patient 12 and through the cranium of patient 12 to access brain 28. IMD 16 can be constructed of a biocompatible material that resists corrosion and degradation from bodily fluids. IMD 16 may comprise a hermetic housing 34 to substantially enclose components, such as a processor, therapy module, and memory.

In the example shown in FIG. 1, leads 20 are implanted within the right and left hemispheres, respectively, of brain 28 in order to deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead that is implanted in one or both hemispheres of brain 28.

Leads 20 may be positioned to deliver electrical stimulation to one or more target tissue sites within brain 28 to manage patient symptoms associated with a disorder of patient 12. Leads 20 may be implanted to position electrodes 24, 26 at desired locations of brain 28 through respective holes in cranium 32. Leads 20 may be placed at any location within brain 28 such that electrodes 24, 26 are capable of providing electrical stimulation to target tissue sites within brain 28 during treatment. Different neurological or psychiatric disorders may be associated with activity in one or more of regions of brain 28, which may differ between patients. For example, a suitable target therapy delivery site within brain 28 for controlling a movement disorder of patient 12 may include one or more of the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, and/or the Field of Forel (thalamic fasciculus). The PPN may also be referred to as the pedunculopontine tegmental nucleus.

As another example, in the case of MDD, bipolar disorder, OCD, or other anxiety disorders, leads 20 may be implanted to deliver electrical stimulation to the anterior limb of the internal capsule of brain 28, and only the ventral portion of the anterior limb of the internal capsule (also referred to as a VC/VS), the subgenual component of the cingulate cortex (which may be referred to as CG25), anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, the habenula, the bed nucleus of the stria terminalis, or any combination thereof. Target tissue sites not located in brain 28 of patient 12 are also contemplated.

As another example, in the case of a seizure disorder or Alzheimer's disease, for example, leads 20 may be implanted to deliver electrical stimulation to regions within the Circuit of Papez, such as, e.g., the anterior thalamic nucleus, the internal capsule, the cingulate, the fornix, the mammillary bodies, the mammillothalamic tract (mammillothalamic fasciculus), and/or hippocampus. For example, in the case of a seizure disorder, IMD 16 may deliver therapy to a region of brain 28 via a selected subset of electrodes 24, 26 to suppress cortical activity within the anterior thalamic nucleus, hippocampus, or other brain region associated with the occurrence of seizures (e.g., a seizure focus of brain 28). Conversely, in the case of Alzheimer's disease, IMD 16 may deliver therapy to a region of brain 28 via electrodes 24, 26 to increase cortical activity within the anterior thalamic nucleus, hippocampus, or other brain region associated with Alzheimer's disease. As another example, in the case of depression (e.g., MDD), IMD 16 may deliver therapy to a region of brain 28 via electrodes 24, 26 to increase cortical activity within one or more regions of brain 28 to effectively treat the patient disorder. As another example, IMD 16 may deliver therapy to a region of brain 28 via electrodes 24, 26 to decrease cortical activity within one or more regions of brain 28, such as, e.g., the frontal cortex, to treat the disorder.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

Leads 20 may be implanted within a desired location of brain 28 via any suitable technique, such as through respective burr holes in the skull of patient 12 or through a common burr hole in the cranium 32. Leads 20 may be placed at any location within brain 28 such that electrodes 24, 26 of leads 20 are capable of providing electrical stimulation to targeted tissue during treatment. Electrical stimulation generated from the stimulation generator (not shown) within the therapy module of IMD 16 may help mitigate the symptoms of movement disorders, such as by improving the performance of motor tasks by patient 12 that may otherwise be difficult. These tasks may include, for example, at least one of initiating movement, maintaining movement, grasping and moving objects, improving gait and balance associated with narrow turns, and the like. The exact therapy parameter values of the stimulation therapy that may help mitigate symptoms of the movement disorder (or other patient condition) may be specific for the particular target stimulation site (e.g., the region of the brain) involved as well as the particular patient and patient condition.

In the examples shown in FIG. 1, electrodes 24, 26 of leads 20 are shown as ring electrodes. Ring electrodes may be relatively easy to program and are typically capable of delivering an electrical field to any tissue adjacent to leads 20. In other examples, electrodes 24, 26 of leads 20 may have different configurations. For example, electrodes 24, 26 of leads 20 may have a complex electrode array geometry that is capable of producing shaped electrical fields, including interleaved stimulation. The complex electrode array geometry may include multiple electrodes (e.g., partial ring or segmented electrodes) around the perimeter of each lead 20, rather than a ring electrode. In this manner, electrical stimulation may be directed to a specific direction from leads 20 to enhance therapy efficacy and reduce possible adverse side effects from stimulating a large volume of tissue. In some examples in which multiple leads 20 are implanted on the same hemisphere surrounding a target, steered electrical stimulation can be performed in between two or more electrodes.

In some examples, outer housing 34 of IMD 16 may include one or more stimulation and/or sensing electrodes. For example, housing 34 can comprise an electrically conductive material that is exposed to tissue of patient 12 when IMD 16 is implanted in patient 12, or an electrode can be attached to housing 34. In other examples, leads 20 may have shapes other than elongated cylinders as shown in FIG. 1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more stimulation therapy programs. A stimulation therapy program may define one or more electrical stimulation parameter values for therapy generated by a therapy module of IMD 16 and delivered from IMD 16 to brain 28 of patient 12. Where IMD 16 delivers electrical stimulation in the form of electrical pulses, for example, the electrical stimulation parameters may include amplitude mode (constant current or constant voltage with or without multiple independent paths), pulse amplitude, pulse rate, pulse width, a waveform shape, and cycling parameters (e.g., with our without cycling, duration of cycling, and the like). In addition, if different electrodes are available for delivery of stimulation, a therapy parameter of a therapy program may be further characterized by an electrode combination, which may define selected electrodes and their respective polarities.

In some examples, IMD 16 is configured to deliver electrical stimulation therapy to brain 28 of patient 12 in an open loop manner, in which IMD 16 delivers the stimulation therapy without intervention from a user or a sensor. The sensor may, for example, provide feedback that may be used to augment the electrical stimulation output from IMD 16. In other examples, IMD 16 is configured to deliver electrical stimulation therapy to brain 28 of patient 12 in a closed loop manner or a pseudo-closed loop manner, in which IMD 16 controls the timing of the delivery and output parameters of the electrical stimulation to brain 28 based on one or more of user input and input from a sensor. For example, in the case of therapy delivery to manage Parkinson's disease, IMD 16 may be configured to deliver electrical stimulation to brain 28 of patient 12 to target a certain minimum reduction in a beta frequency band of a sensed bioelectrical brain signal, a certain increase in a gamma frequency band of a sensed bioelectrical brain signal, or both.

In addition to being configured to deliver therapy to manage a disorder of patient 12, therapy system 10 is configured to sense bioelectrical brain signals of patient 12. For example, IMD 16 may include a sensing module that is configured to sense bioelectrical brain signals within one or more regions of brain 28 via a subset of electrodes 24, 26, another set of electrodes, or both. Accordingly, in some examples, electrodes 24, 26 may be used to deliver electrical stimulation from the therapy module to target sites within brain 28 as well as sense brain signals within brain 28. However, IMD 16 can also use a separate set of sensing electrodes to sense the bioelectrical brain signals. In the example shown in FIG. 1, the signals generated by electrodes 24, 26 are conducted to the sensing module within IMD 16 via conductors within the respective lead 20A, 20B. In some examples, the sensing module of IMD 16 may sense bioelectrical brain signals via one or more of the electrodes 24, 26 that are also used to deliver electrical stimulation to brain 28. In other examples, one or more of electrodes 24, 26 may be used to sense bioelectrical brain signals while one or more different electrodes 24, 26 may be used to deliver electrical stimulation.

Depending on the particular stimulation electrodes and sense electrodes used by IMD 16, IMD 16 may monitor bioelectrical brain signals and deliver electrical stimulation at the same region of brain 28 or at different regions of brain 28. In some examples, the electrodes used to sense bioelectrical brain signals may be located on the same lead used to deliver electrical stimulation, while in other examples, the electrodes used to sense bioelectrical brain signals may be located on a different lead than the electrodes used to deliver electrical stimulation. In some examples, a bioelectrical brain signal of patient 12 may be monitored with external electrodes, e.g., scalp electrodes. Moreover, in some examples, the sensing module that senses bioelectrical brain signals of brain 28 (e.g., the sensing module that generates an electrical signal indicative of the activity within brain 28) is in a physically separate housing from outer housing 34 of IMD 16. However, in the example shown in FIG. 1 and the example primarily referred to herein for ease of description, the sensing module and therapy module of IMD 16 are enclosed within a common outer housing 34.

The bioelectrical brain signals sensed by IMD 16 may reflect changes in electrical current produced by the sum of electrical potential differences across brain tissue. Example bioelectrical brain signals include, but are not limited to, an electroencephalogram (EEG) signal, an electrocorticogram (ECoG) signal, a local field potential (LFP) sensed from within one or more regions of a patient's brain and/or action potentials from single cells within the patient's brain. In some examples, LFP data can be measured ipsilaterally or contralaterally and considered as an average (e.g., a maximum or minimum or a heuristic combination thereof) or as some other value. The location at which the signals are obtained may be adjusted to a disease onset side of the body of patient 12 or severity of symptoms or disease duration. The adjustments, may, for example, be made on the basis of clinical symptoms presented and their severity, which can be augmented or annotated with recorded LFP data. A clinician or a processor of IMD 16 may also add heuristic weights to ipsilaterally and/or contralaterally measured LFP data to be considered for system feedback.

Sensed bioelectrical brain signals of patient 12 may be used to characterize the brain state of patient 12. As described in further detail below, in some examples, a processor of IMD 16 or another device (e.g., programmer 14) is configured to control delivery of a notification to patient 12 based on a sensed bioelectrical brain signal. In one example, the processor may sense a bioelectrical brain signal within brain 28 of patient 12 and generate a notification to patient 12 or a caretaker of patient 12 that indicates an efficacy of the therapy currently being delivered to patient 12 according to a particular set of one or more therapy parameter values may have changed, such that evaluation of the one or more therapy programs may be desirable, e.g., to improve the efficacy of the therapy, based on the sensed bioelectrical brain signal. For example, in response to detecting a bioelectrical brain signal having a biomarker associated with the notification, processor may generate the notification.

In some examples, the biomarker includes a particular signal characteristic, such as, but not limited to, any one or more of a time domain characteristic of a bioelectrical brain signal (e.g., a mean, median, peak or lowest amplitude, instantaneous amplitude, waveform morphology, pulse frequency or pulse to pulse variability), a frequency domain characteristic of a bioelectrical brain signal (e.g., an energy level in one or more frequency bands), a pattern of the bioelectrical brain signal over time, or some other measurable characteristic of a sensed bioelectrical brain signal. In some cases, the biomarker may be considered the absence of a particular characteristic (e.g., the energy level in a particular frequency band is not over a threshold level). The presence or absence of a signal characteristic may be indicative of a particular patient state, such that when a sensed bioelectrical brain signal includes, or in some cases, does not include, the signal characteristic, the sensed bioelectrical brain signal may indicate patient 12 is in a state in which the effects of therapy may have changed, e.g., diminished relative to a baseline state in which the efficacious therapy was observed. The biomarker may be specific to patient 12, a patient condition, or both, such that the biomarkers based on which the notifications are generated may differ between patients.

In some examples, in order to determine whether a sensed bioelectrical brain signal includes the biomarker, the processor may compare a time domain characteristic (e.g., an amplitude) of the sensed bioelectrical brain signal with a stored value, compare a particular power level within a particular frequency band of the bioelectrical brain signal to a stored value, determine whether the sensed bioelectrical brain signal substantially correlates to a template, or combinations thereof. For example, the processor may determine one or more frequency band characteristics of a sensed bioelectrical brain signal and determine the sensed bioelectrical brain signal includes the biomarker in response to determining the one or more frequency band characteristics meet a particular set of criteria associated with generating the notification. As an example, in response to determining a sensed bioelectrical brain signal has a beta band power level that is greater than the beta band power level of a baseline bioelectrical brain signal, and a gamma band power level that is less than the gamma band power level of the baseline bioelectrical brain signal, the processor may determine the sensed bioelectrical brain signal includes a biomarker that indicates a change in efficacy of therapy delivered by IMD 16 (relative to the baseline state). In this case, the biomarker includes the above-identified power level conditions in the beta and gamma bands. As another example, the processor may determine the sensed bioelectrical brain signal includes the biomarker in response to determining the sensed bioelectrical brain signal does not substantially correlate (e.g., correlate or nearly correlate) with a template signal. Other techniques are also contemplated.

The biomarker may be determined based on a bioelectrical brain signal sensed when therapy delivery by IMD 16 was determined to be efficacious, e.g., based on a subjective patient 12 rating or other patient input, based on a sensed parameter (e.g., a physiological signal or based on a patient activity level determined based on signals generated by one or more motion sensors), or any other technique or combinations of techniques. In some examples, a processor may determine the biomarker by at least determining a first signal characteristic of a bioelectrical brain signal sensed when therapy delivery by IMD 16 was determined to be efficacious. The first signal characteristic may be indicative of a patient state in which IMD 16 is delivering efficacious therapy to patient 12 and the biomarker may be selected to be indicative of a patient state in which therapy delivery by IMD 16 is not sufficiently efficacious. In this example, the biomarker may be a signal characteristic of a sensed bioelectrical brain signal that is not equal to the first signal characteristic and is outside of a tolerance range defined relative to the first signal characteristic. For example, if the first signal characteristic is a first power level within a beta band of a sensed bioelectrical brain signal, a biomarker may be a power level within the beta band that is not equal to the first power level or any value within a tolerance range of the first power level.

In another example, a processor may determine the biomarker by at least determining a second signal characteristic of a bioelectrical brain signal sensed when patient 12 is in a state in which efficacious effects of therapy delivery by IMD 16 are not observed (e.g., a state prior to any therapy delivery by IMD 16 or a state in which IMD 16 is otherwise not delivering therapy to patient 12). Again, the biomarker may be selected to be indicative of a patient state in which therapy delivery by IMD 16 is not sufficiently efficacious. Thus, in this example, the biomarker may be the second signal characteristic and values within a tolerance range of the second signal characteristic (e.g., the tolerance range measured relative to the second signal characteristic defines a range of values for the biomarker). For example, if the second signal characteristic is a second power level within a beta band of a sensed bioelectrical brain signal, a biomarker may be a power level within the beta band that is equal to the second power level or any value within a tolerance range of the second power level.

The tolerance range (also referred to as a tolerance band in some examples) may be predetermined in some examples. In addition, the tolerance range may be selected by a clinician in some examples. The size of the tolerance range may vary depending on one or more factors, such as the severity of the patient condition, the type of patient condition, patient preference (e.g., the level of symptoms patient 12 can tolerate), clinician preference, or any combination of these factors.

In some examples, IMD 16 may be configured to sense the bioelectrical brain signal (e.g., by measuring a LFP) at periodic, predetermined (which may also be periodic), or random intervals, or in response to a patient input or another trigger. In other examples, IMD 16 continuously senses the bioelectrical brain signal, but the processor only samples the sensed bioelectrical brain signal (e.g., the last stored bioelectrical brain signal) and determines whether the sample includes the biomarker at predetermined periodic times or in response to user input (e.g., input/trigger from a patient).

In response to receiving the notification generated by the processor of IMD 16 or another device (e.g., programmer 14), patient 12 may schedule a visit with a clinician. The visit with the clinician may be desirable to, for example, reassess the efficacy of therapy delivery by IMD 16 and, in some cases, change the therapy regimen selected for patient 12. During the patient's visit with the clinician, the clinician may reprogram IMD 16 (during a programming session), such as by modifying at least one therapy parameter value (e.g., by modifying one or more therapy parameter values of a therapy program stored by IMD 16 or by programming IMD 16 with new therapy programs).

The therapy parameter values of the electrical stimulation therapy that may help mitigate symptoms of the movement disorder (or other patient condition) may be specific for the particular target stimulation site (e.g., the region of the brain) involved as well as the particular patient and patient condition. In some cases, the efficacy of therapy delivery to patient 12 according to a particular therapy program may change over time as a result of a change in the patient condition (e.g., due to an improvement or worsening of the symptoms), as a result of migration of one or both leads 20A, 20B from a target therapy delivery site, a change in the medications taken by patient 12, tolerance to specific stimulation parameters, disease progression, adaptation (or accommodation) to the therapy, desensitization to the therapy, or other reasons. As a result, one or more therapy programs with which IMD 16 generates and delivers therapy to patient 12 may become less efficacious over time. By generating a notification to patient 12 in response to detecting a biomarker indicative of a possible change in the efficacy of therapy delivery, therapy system 10 is configured to actively manage when IMD 16 may need to be reprogrammed or at least reassessed by a clinician.

In addition, automatically generating a notification to patient 12 to schedule a visit with a clinician may help the clinician prioritize patients; patients for which the biomarkers have been detected may have more of a need of therapy evaluation than patients for which the biomarkers have not been detected. In this way, detection of a biomarker by IMD 16 may be used to qualify patients prior to seeing a clinician, and may also help reduce the frequency with which a patient visits the clinician by triggering the patient's initiation of the therapy session in response to detection of a biomarker that indicates efficacy of therapy may have changed. Moreover, therapy system 10 that is configured to generate, based on a sensed bioelectrical brain signal, a notification to patient 12 to schedule a visit with a clinician may help reduce the frequency of patient visits to a clinician's office by helping patient 12 determine when the visit may be desirable.

In some examples, the processor is configured to generate a notification based on a sensed bioelectrical brain signal that has a relatively high confidence level. Thus, the processor may first determine whether the confidence level of a bioelectrical brain signal meets a certain threshold (e.g., a predetermined threshold). The confidence level of a sensed bioelectrical brain signal may be determined by the processor using any suitable technique. In some examples, the processor determines the confidence level based on the consistency of the measured signal (e.g., determined based on the variability of the signal over a period of time or a number of sampling periods), signal strength, background noise level, or any combination thereof. In some examples, in response to determining the confidence level is relatively high (e.g., the variability of the signal is less than or equal to a predetermined threshold, the signal strength is greater than or equal to a predetermined threshold, a background noise level is less than or equal to a predetermined threshold, or any combination thereof), the processor may determine whether the bioelectrical brain signal includes the biomarker associated with the notification, and generate the notification in response to determining the bioelectrical brain signal includes the biomarker associated with the notification.

In some examples, in response to determining the confidence level of a sensed bioelectrical brain signal is relatively low (e.g., the variability of the signal is greater than or equal to a predetermined threshold, the signal strength is less than or equal to a predetermined threshold, a background noise level is greater than or equal to a predetermined threshold, or any combination thereof), the processor may not generate a notification and may, instead, attempt to sense a bioelectrical brain signal with a relatively high confidence level before taking a responsive action, such as generating the notification. For example, the processor may control the sensing module of IMD 16 (or a separate sensing module) to sense a bioelectrical brain signal at a subsequent time and determine the confidence level in the subsequently sensed bioelectrical brain signal. For example, the processor may control the sensing module to sense a bioelectrical brain signal at predetermined intervals or in response to patient input until a bioelectrical brain signal with a relatively high confidence level is sensed or a number or percentage of signals that have a relatively high confidence level are sensed, or until a threshold number of sense attempts have been reached.

In response to determining the confidence level of one sensed signal or a plurality of sensed signals over time (e.g., a threshold number of sensed signals) is relatively low the processor may take one or more responsive actions. In some examples, the processor may store the sensed signals in a memory of IMD 16 or another component (e.g., programmer 14) for later retrieval and analysis by the clinician. In addition or instead, in some examples, the processor may generate a notification to the patient (or patient caretaker) that a visit to the clinician is recommended and cause IMD 16 to revert to a known safe mode. The safe mode may be a set of parameters that is known to provide a safe and comfortable therapy to patient 16 from IMD 12. The safe mode may be customizable and may be device, clinician, therapy and/or patient specific. The safe mode may be configurable during device or application setup and may depend upon the patient needs and/or the type of therapy delivered by IMD 16.

In some examples, a processor of system 10 (e.g., of IMD 16 or programmer 14) is configured to generate and present a graphical user interface that correlates sensed bioelectrical brain signals with time and date stamps that indicate the time at which the bioelectrical brain signal was measured, and, in some examples, the time at which a biomarker was detected by system 10. This graphical user interface may provide, to the clinician, information that may be useful for reprogramming IMD 16 or at least assessing the efficacy of therapy delivery by IMD 16 or the patient condition.

In some cases, if patient 12 is prescribed a medical regimen (e.g., a pharmaceutical drug) in addition to receiving electrical stimulation therapy from IMD 16, patient 12 may provide input to IMD 16 or programmer 14 (or another device) that indicates when patient 12 complied with the medical regimen (e.g., input the time and date that the drug was taken). In response, the processor of system 10 may generate a compliance marker indicating when patient 12 complied with a medical regimen, and the processor may store the compliance marker in a memory of system 10 (e.g., a memory of IMD 16 or programmer 14). The processor may also include this information in the graphical user interface. The processor may, for example, generate a display (e.g., graphical or textual) that visually correlates the compliance markers with the bioelectrical brain signals with time and date stamps. The clinician may quickly ascertain, based on the display, whether patient 12 was complying with the prescribed medical regimen.

Therapy data that associates compliance markers with the sensed bioelectrical brain signals (e.g., temporally correlated compliance markers and bioelectrical brain signals, biomarkers, or both) may help a clinician, alone or with the aid of a processor (e.g., of programmer 14) determine whether a detected biomarker was attributable to the patient's lack of compliance with the medical regimen. Thus, the information regarding the compliance of patient 12 with the medical regimen may indicate whether patient 12 may need to improve compliance with the medical regimen in order to improve the efficacy of therapy system 10, instead of or in addition to reprogramming IMD 16. Accordingly, evaluating patient compliance with a medication regimen may help reduce the possibility that the intensity of electrical stimulation delivered by IMD 16 is unnecessarily increased in an attempt to improve therapeutic efficacy of system 10. Decreasing the intensity of electrical stimulation may help reduce current drain on a power source of IMD 16, increase the efficiency of the power source, decrease the adaptation of patient 12 to the therapy delivery, or any combination thereof. Intensity of electrical stimulation may be a function of one or more stimulation parameter values, such as current amplitude, voltage amplitude, frequency, cycling parameters, number of active electrodes, and, in the case of stimulation pulses, pulse width.

In some examples, a processor of system 10, such as a processor of IMD 16, programmer 14, another device, or any combination thereof, may be configured to modify therapy delivered by IMD 16 in response to detecting the biomarker. In response to determining the modification to the therapy does not improve the efficacy of the therapy provided by IMD 16, e.g., such that the biomarker is still detected after modifying the therapy, the processor may generate a notification.

The processor may modify the therapy delivered by IMD 16 using any suitable technique. In some examples, the processor modifies therapy by at least modifying at least one therapy parameter value with which IMD 16 generates and delivers therapy to patient 12. The at least one therapy parameter value may be a part of a therapy program that defines values for a plurality of therapy parameters. As a result, in some examples, the processor may modify at least one therapy parameter value by at least modifying a therapy program (e.g., changing the value of at least one therapy parameter of the therapy program or selecting a new therapy program).

In some examples, the processor may make a first modification to a therapy program currently implemented by IMD 16 to deliver therapy to patient 12, and then determine whether the therapy delivery by IMD 16 according to the modified therapy program was efficacious. The processor may determine whether the modified therapy program was efficacious by, for example, determining whether a sensed bioelectrical brain signal includes the biomarker. If, for example, the processor does not detect the biomarker in a bioelectrical brain signal sensed after IMD 16 delivers therapy to patient 12 according to the modified therapy program, the processor may determine that therapy delivery according to the modified therapy program was efficacious (e.g., resulted in a certain reduction in beta band activity for a patient with Parkinson's disease), such that a programming session with a clinician to improve the efficacy of therapy delivery by IMD 16 may no longer be desirable to improve the efficacy of therapy. In this way, the processor may control therapy delivery by IMD 16 in a closed-loop or pseudo-closed-loop manner based on a sensed bioelectrical brain signal. In some examples, the processor may only control therapy delivery by IMD 16 in this closed-loop or pseudo-closed-loop manner if the confidence level in the sensed bioelectrical brain signal is sufficiently high, as described above.

On the other hand, if the processor detects the biomarker in a bioelectrical brain signal sensed after IMD 16 delivers therapy to patient 12 according to the modified therapy program, the processor may determine that therapy delivery according to the modified therapy program did not meet a desired level of efficacy, such that a programming session with a clinician may be advisable. Accordingly, in some examples, the processor may generate a notification in response to determining the biomarker was present in a bioelectrical brain signal sensed after IMD 16 delivers therapy to patient 12 according to the modified therapy program.

In some examples, the processor may repeat the process of modifying a therapy program and determining the efficacy of the modified therapy program for a predetermined number of iterations, such as one, two, three, four or more. If, after the predetermined number of iterations, the modified therapy program does not result in efficacious therapy delivery, e.g., as indicated by the presence of the biomarker in a sensed bioelectrical brain signal, the processor may generate the notification.

External programmer 14 wirelessly communicates with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. In addition, or instead, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20, the arrangement of electrodes 24, 26 on leads 20, the position of leads 20 within brain 28, initial programs defining therapy parameter values, and any other information that may be useful for programming into IMD 16. Programmer 14 may also be capable of completing functional tests (e.g., measuring the impedance of electrodes 24, 26 of leads 20).

The clinician may also generate and store therapy programs within IMD 16 with the aid of programmer 14. During a programming session, the clinician may determine one or more therapy programs that may provide efficacious therapy to patient 12 to address symptoms associated with the movement disorder (or other patient conditions). For example, the clinician may select one or more electrode combinations with which stimulation is delivered to brain 28. During the programming session, patient 12 may provide feedback to the clinician as to the efficacy of the specific program being evaluated or the clinician may evaluate the efficacy based on one or more sensed or observable physiological parameters of patient (e.g., muscle activity) or based on motion detected via one or more motion sensors that generate signals indicative of motion of patient 12. Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter, or allow the patient 12 to select between different therapy groups each having independent therapy parameters for specific symptoms or activities (e.g., walking, speech, tremor, and the like).

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

Figure 2:
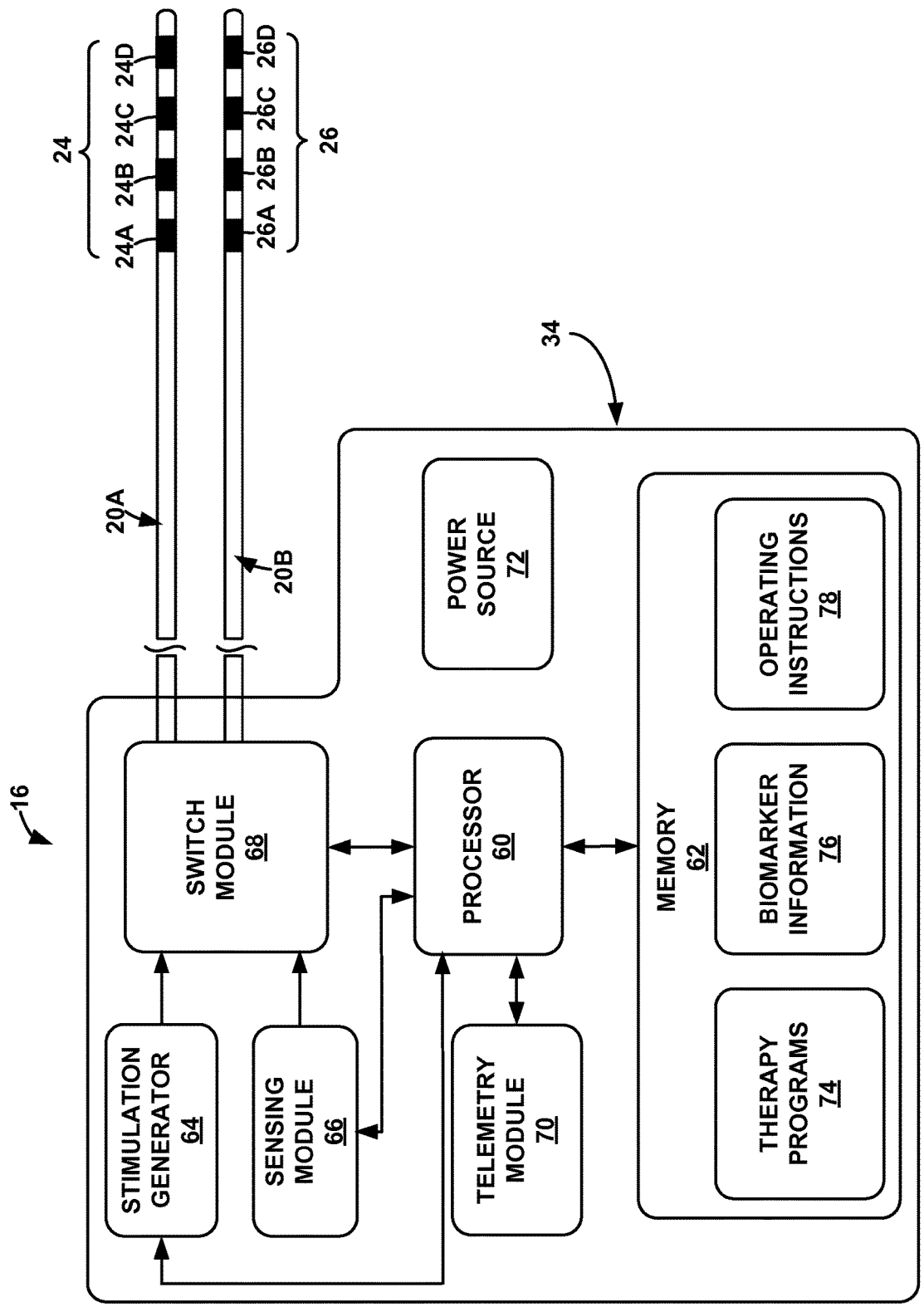
FIG. 2 is functional block diagram illustrating components of an example medical device.

FIG. 2 is functional block diagram illustrating components of an example IMD 16. In the example shown in FIG. 2, IMD 16 includes processor 60, memory 62, stimulation generator 64, sensing module 66, switch module 68, telemetry module 70, and power source 72. Memory 62, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

In the example shown in FIG. 2, memory 62 stores therapy programs 74, biomarker information 76, and operating instructions 78, e.g., in separate memories within memory 62 or separate areas within memory 62. Each stored therapy program 74 defines a particular program of therapy in terms of respective values for electrical stimulation parameters, such as a stimulation electrode combination, electrode polarity, current or voltage amplitude, and, if stimulation generator 64 generates and delivers stimulation pulses, the therapy programs may define values for a pulse width, and pulse rate of a stimulation signal. Each stored therapy program 74 may also be referred to as a set of therapy parameter values. In some examples, the therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Biomarker information 76 stored by memory 62 includes one or more biomarkers that indicate therapy delivery by IMD 16 may have changed, e.g., relative to a baseline patient state. In some examples, biomarker information 76 may store a threshold amplitude value, and any amplitude that is greater than or equal to the threshold amplitude value may be a biomarker. In other examples, any amplitude that is less than or equal to the threshold amplitude value may be a biomarker. Other types of biomarker information 76 may also be stored instead of or in addition to the threshold amplitude value. For example, biomarker information 76 may include a threshold power level in a frequency band, and any sensed bioelectrical brain signal that has a power level in the frequency band that is outside a tolerance range of the stored threshold power level may include a biomarker that indicates therapy delivery by IMD 16 may have changed. Other types of biomarker information 76 may be stored.

In some examples, memory 62 also stores one or more baseline bioelectrical brain signals that indicate the baseline patient state, in which therapy delivery by IMD 16 is efficacious in reducing or even eliminating one or more symptoms of the patient condition. A baseline bioelectrical brain signal which may be signals that were sensed by sensing module 66 or another sensing module 66 when therapy delivered to patient 12 by IMD 16 was determined to be efficacious, e.g., based on patient input or based on one or more sensed patient parameters (e.g., a physiological parameter, patient motion, or patient activity level). As discussed in further detail with respect to FIG. 8, the baseline bioelectrical brain signal may be used to determine biomarker information 76.

In some examples, memory 62 may also store brain signal data generated by sensing module 66 via at least one of electrodes 24, 26 and, in some cases, at least a portion of outer housing 34 of IMD 16, an electrode on outer housing 34 of IMD 16 or another reference. For example, the bioelectrical brain signals generated by one or more of the electrodes 24, 26 that indicates an efficacy of therapy delivery by IMD 16 may be stored by memory 62. In addition, in some examples, processor 60 may append biomarker information 76 with a time and date stamp, sensed patient motion or posture information from a motion sensor (e.g., incorporated in IMD 16 or otherwise communicatively coupled to IMD 16), or both.

Operating instructions 78 guide general operation of IMD 16 under control of processor 60, and may include instructions for monitoring brains signals within one or more brain regions via electrodes 24, 26 and/or selecting one or more therapy cycle parameters based on the monitored brain signals.

Stimulation generator 64, under the control of processor 60, generates stimulation signals for delivery to patient 12 via selected combinations of electrodes 24, 26. In some examples, stimulation generator 64 generates and delivers stimulation signals to one or more target regions of brain 28 (FIG. 1), via a select combination of electrodes 24, 26, based on one or more stored therapy programs 74. The target tissue sites within brain 28 for stimulation signals or other types of therapy and stimulation parameter values may depend on the patient condition for which therapy system 10 is implemented to manage. While stimulation pulses are described, stimulation signals may be of any form, such as continuous-time signals (e.g., sine waves) or the like.

The processors described in this disclosure, including processor 60, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processor 60 is configured to control stimulation generator 64 according to therapy programs 74 stored in memory 62 to apply particular stimulation parameter values specified by one or more programs, such as amplitude, pulse width, and pulse rate.

In the example shown in FIG. 2, the set of electrodes 24 of lead 20A includes electrodes 24A, 24B, 24C, and 24D, and the set of electrodes 26 of lead 20B includes electrodes 26A, 26B, 26C, and 26D. Processor 60 may control switch module 68 to apply the stimulation signals generated by stimulation generator 64 to selected combinations of electrodes 24, 26. In particular, switch module 68 may couple stimulation signals to selected conductors within leads 20, which, in turn, deliver the stimulation signals across selected electrodes 24, 26. Switch module 68 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 64 is coupled to electrodes 24, 26 via switch module 68 and conductors within leads 20. In some examples, however, IMD 16 does not include switch module 68.

Stimulation generator 64 may be a single channel or multi-channel stimulation generator. In particular, stimulation generator 64 may be capable of delivering, a single stimulation pulse, multiple stimulation pulses or continuous signal at a given time via a single electrode combination or multiple stimulation pulses at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12.

Sensing module 66, under the control of processor 60, is configured to sense bioelectrical brain signals of patient 12 via a selected subset of electrodes 24, 26 or with one or more electrodes 24, 26 and at least a portion of a conductive outer housing 34 of IMD 16, an electrode on an outer housing of IMD 16 or another reference. Processor 60 may control switch module 68 to electrically connect sensing module 66 to selected electrodes 24, 26. In this way, sensing module 66 may selectively sense bioelectrical brain signals with different combinations of electrodes 24, 26 (and/or a reference other than an electrode 24, 26). As previously described, processor 60 may monitor the efficacy of therapy delivery by IMD 16 via the sensed bioelectrical brain signals and determine whether the efficacy of therapy delivery has changed, and, in response, generate a notification (e.g., to patient 12 or patient caretaker).

Although sensing module 66 is incorporated into a common housing 34 with stimulation generator 64 and processor 60 in FIG. 2, in other examples, sensing module 66 is in a separate outer housing from outer housing 34 of IMD 16 and communicates with processor 60 via wired or wireless communication techniques.

In some examples, as discussed in further detail below with respect to FIGS. 9 and 10, processor 60 (or another processor of system 10) may be configured to modify therapy delivered by IMD 16 in response to detecting a biomarker in a bioelectrical brain signal sensed by sensing module 66. Processor 60 may, for example, modify a therapy program with which stimulation generator 64 generates and delivers electrical stimulation signals, determine whether the modification to the therapy changes the efficacy of the therapy provided by IMD 16, e.g., determines whether the biomarker is detected after modifying the therapy, and generate a notification in response to determining the modification to the therapy did not sufficiently improve the efficacy of the therapy (e.g., the biomarker is still detected after modifying the therapy delivery). In this way, physiological signal sensed by sensing module 66 may be used for closed-loop control of electrical stimulation delivery by IMD 16.

Telemetry module 70 supports wireless communication between IMD 16 and an external programmer 14 or another computing device under the control of processor 60. Processor 60 of IMD 16 may receive, as updates to programs, values for various stimulation parameters such as amplitude and electrode combination, from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14. For example, processor 60 may transmit brain state information 76 to programmer 14 via telemetry module 70.

Power source 72 delivers operating power to various components of IMD 16. Power source 72 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
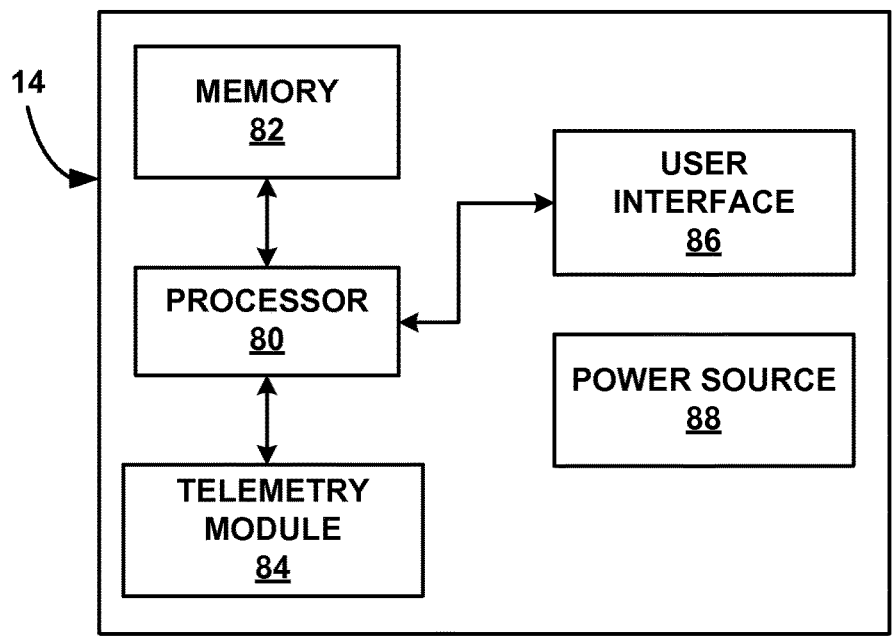
FIG. 3 is a functional block diagram illustrating components of an example medical device programmer.

FIG. 3 is a functional block diagram illustrating components of an example medical device programmer 14 (FIG. 1). Programmer 14 includes processor 80, memory 82, telemetry module 84, user interface 86, and power source 88. Processor 80 controls user interface 86 and telemetry module 84, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80.

A user, such as a clinician or patient 12, may interact with programmer 14 through user interface 86. User interface 86 includes a display (not shown), such as a LCD or LED display or other type of screen, with which processor 80 may present information related to the therapy, such as a notification that indicates efficacy of therapy delivery by IMD 16 may have changed, e.g., a notification that an appointment with a clinician is recommended, or therapy data (e.g., a waveform of a sensed bioelectrical brain signal correlated with medication inputs from patient 12). In addition, processor 80 may control the display to present information related to bioelectrical signals sensed via a plurality of sense electrode combinations. In addition, user interface 86 may include an input mechanism to receive input from the user. The input mechanisms may include, for example, buttons, a keypad (e.g., an alphanumeric keypad), a peripheral pointing device or another input mechanism that allows the user to navigate though user interfaces presented by processor 80 of programmer 14 and provide input.

If programmer 14 includes buttons and a keypad, the buttons may be dedicated to performing a certain function, i.e., a power button, or the buttons and the keypad may be soft keys that change function depending upon the section of the user interface currently viewed by the user. In addition, or instead, the screen (not shown) of programmer 14 may be a touch screen that allows the user to provide input directly to the user interface shown on the display. The user may use a stylus or their finger to provide input to the display. In other examples, user interface 86 also includes audio circuitry for providing audible notifications, instructions or other sounds to patient 12, receiving voice commands from patient 12, which may be useful if patient 12 has limited motor functions, or both. Patient 12, a clinician or another user may also interact with programmer 14 to manually select therapy programs, generate new therapy programs, modify therapy programs through individual or global adjustments, and transmit the new programs to IMD 16.

In some examples, at least some of the control of therapy delivery by IMD 16 may be implemented by processor 80 of programmer 14. For example, in some examples, processor 80 may receive sensed brain signal information from IMD 16 or from a sensing module that is separate from IMD 16. The separate sensing module may, but need not be, implanted within patient 12. Brain signal information may include, for example, a time domain characteristic (e.g., an amplitude) or a frequency domain characteristic (e.g., an energy level in one or more frequency bands) of brain signals monitored by sensing module 66 using one or more of electrodes 24, 26 (FIG. 2). Based on the monitored brain signal information, processor 80 may determine whether the efficacy of therapy delivery by IMD 16 may have changed relative to a baseline state and generate a notification based in response to determining the efficacy of therapy delivery by IMD 16 may have changed relative to the baseline state.

Figure 9:
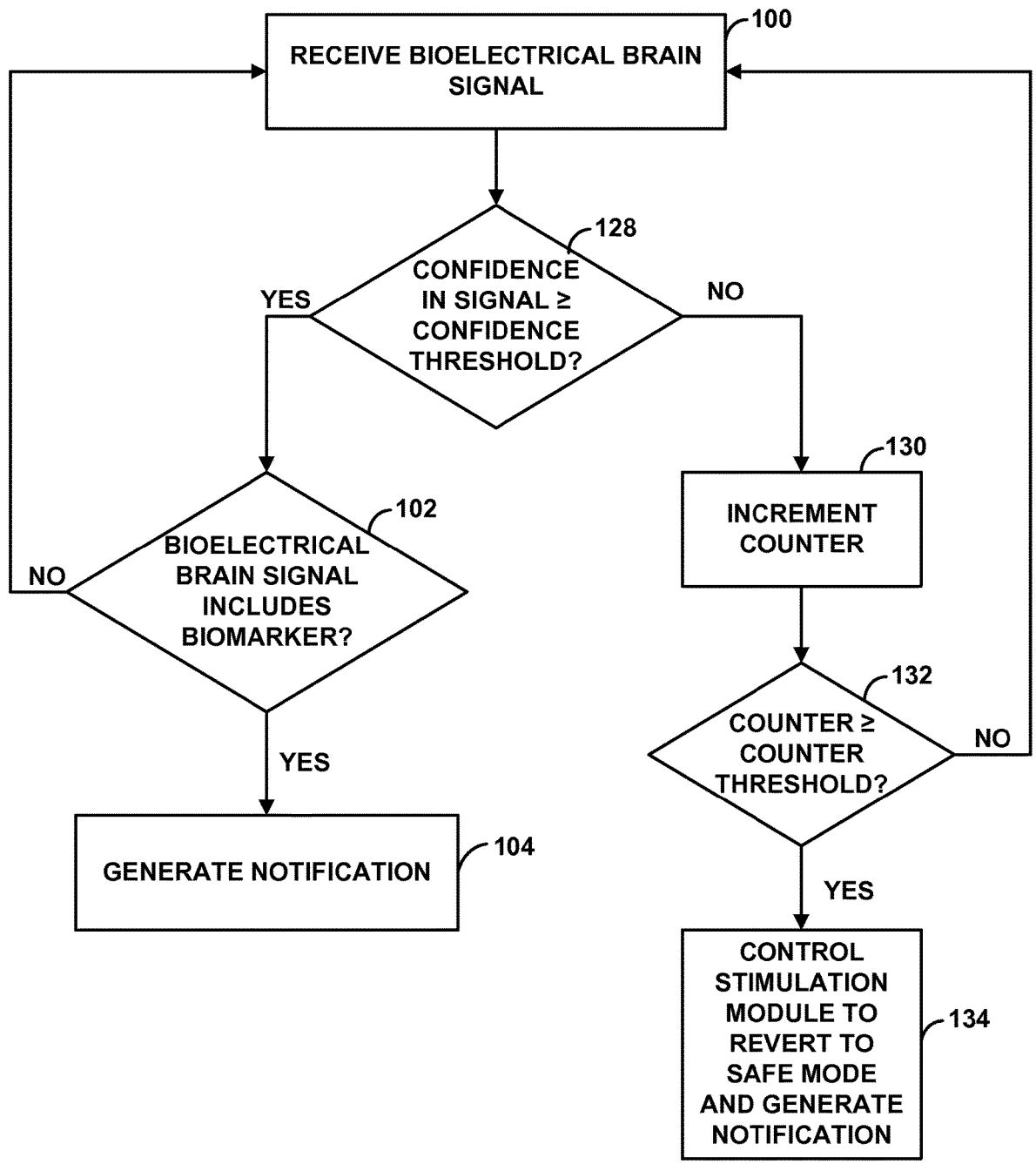
FIG. 9 is a flow diagram illustrating another example technique for generating a notification that indicates efficacy of one or more therapy parameters with which therapy is delivered to a patient may have changed.
Figure 10:
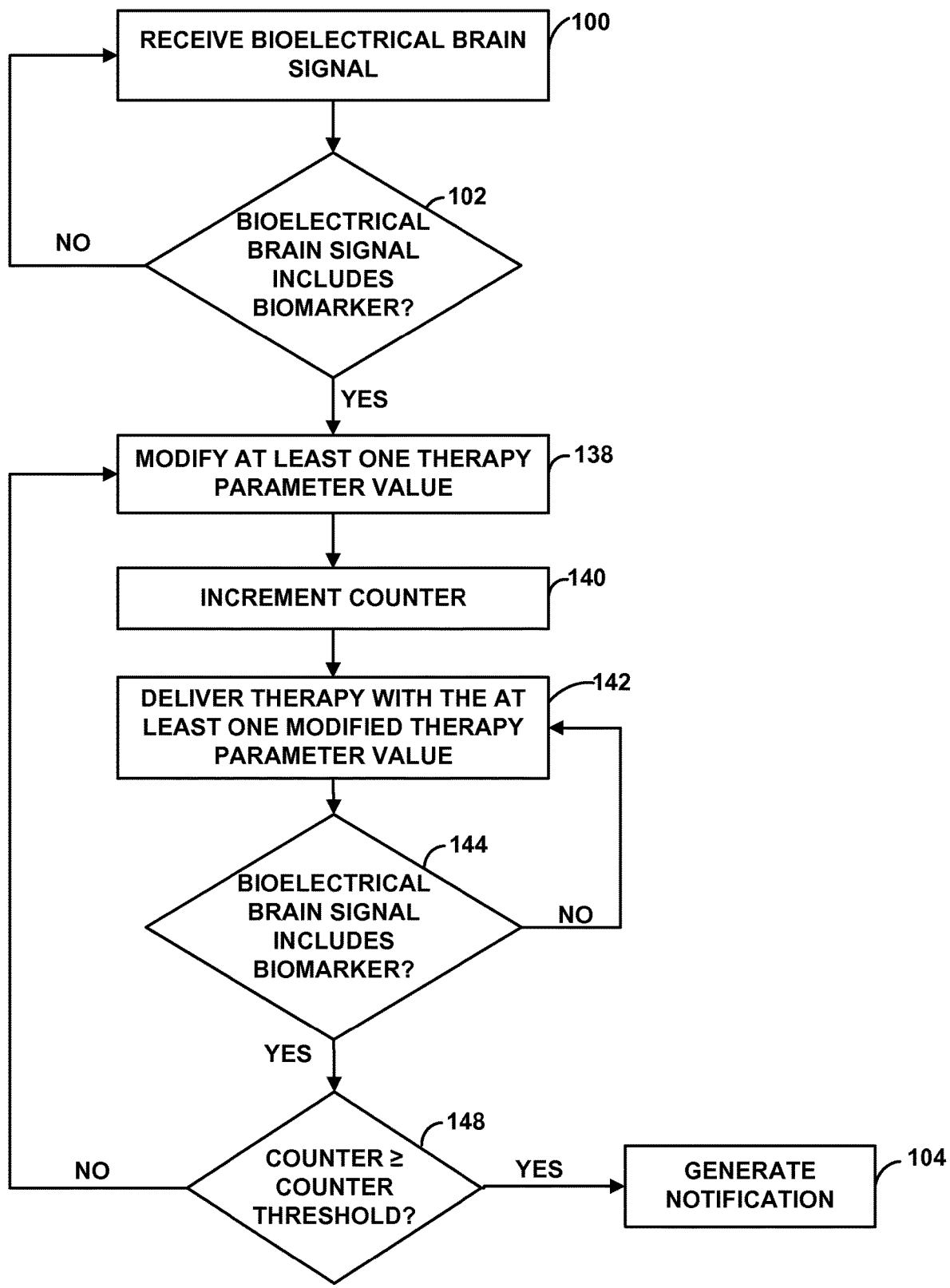
FIG. 10 is a flow diagram illustrating an example technique for adjusting therapy delivery by a medical device based on a sensed bioelectrical brain signal.

In addition, in some examples, based on the monitored brain signal information, processor 80 may determine the brain state of patient 12 and control delivery of therapy from IMD 16 to patient 12 based on the determined brain state, e.g., as described with respect to FIGS. 9 and 10.

Memory 82 may include instructions for operating user interface 86 and telemetry module 84, and for managing power source 88. Memory 82 may also store any therapy data retrieved from IMD 16 during the course of therapy, biomarker information, sensed bioelectrical brain signals, and the like. The clinician may use this therapy data to determine the progression of the patient condition in order to plan future treatment for the movement disorder (or other patient condition) of patient 12. Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 84. Accordingly, telemetry module 84 may be similar to the telemetry module contained within IMD 16. In other examples, programmer 14 may be capable of infrared communication or direct communication through a wired connection. In this manner, other external devices may be capable of communicating with programmer 14 without needing to establish a secure wireless connection.

Power source 88 is configured to deliver operating power to the components of programmer 14. Power source 88 may include a battery and a power generation circuit to produce the operating power. In some examples, the battery may be rechargeable to allow extended operation. Recharging may be accomplished by electrically coupling power source 88 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate.

Figure 4:
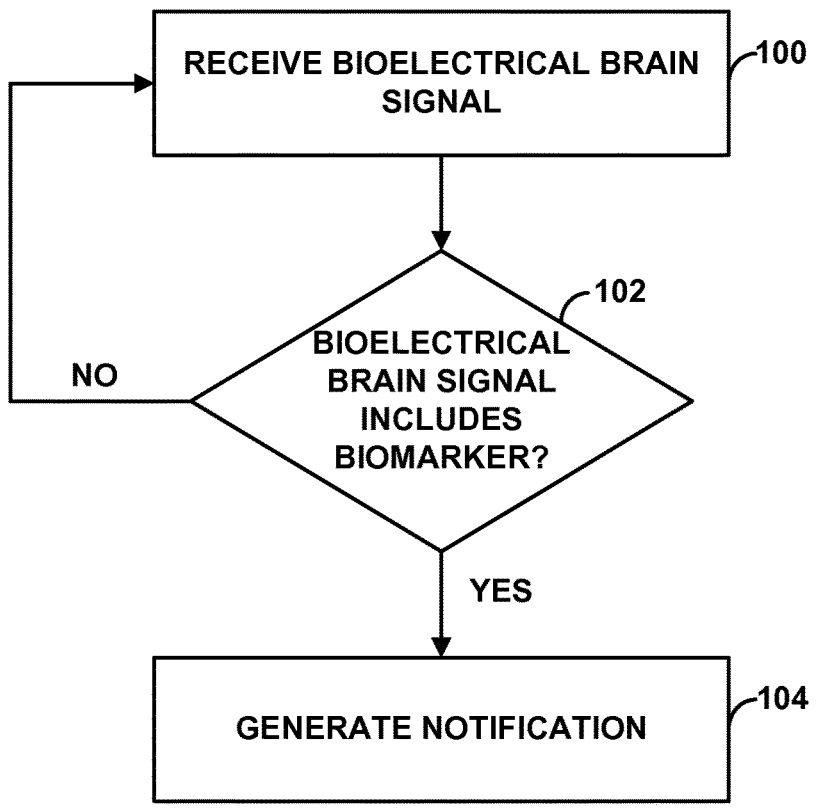
FIG. 4 is a flow diagram illustrating an example technique for generating a notification that indicates efficacy of one or more therapy parameters with which therapy is delivered to a patient may have changed.

FIG. 4 is a flow diagram illustrating an example technique for generating a notification that indicates efficacy of therapy delivery by IMD 16 may have changed. The notification may be received by patient 12 or a patient caretaker. In response to receiving the notification, patient 12 (or patient caretaker) may take a responsive action, such as scheduling an appointment with a clinician, who may evaluate the one or more therapy programs with which IMD 16 generates and delivers therapy to patient 12 and, in some cases, modify at least one therapy program in order to increase the efficacy of the therapy delivery to patient 12. In addition, or instead, the notification may be received by a clinician, who may then take a responsive action, such as contacting patient 12 to schedule an appointment. While the technique shown in FIG. 4, as well as many other figures (e.g., FIGS. 5 and 7-10) are described with respect to processor 60 of IMD 16, in other examples, a processor of another device, such as processor 80 of programmer 14 (FIG. 3) can perform any part of the techniques described herein, alone or in combination with another device.

In accordance with the technique shown in FIG. 4, processor 60 of IMD 16 receives a bioelectrical brain signal sensed by sensing module 66 (100). For example, processor 60 may control sensing module 66 to sense a brain signal of patient 12, e.g., via one or more of electrodes 24, 26 on leads 20, and sensing module 66 may transmit the sensed bioelectrical brain signal to processor 60. In some examples, processor 60 receives the bioelectrical brain signal sensed by sensing module 66 at randomly or pseudo-randomly selected times, predetermined intervals, while in other examples, processor 60 receives the bioelectrical brain signal sensed by sensing module 66 at random intervals. The frequency with which processor 60 receives the bioelectrical brain signal sensed by sensing module 66 may be selected by a clinician in some examples.

While some portions of the disclosure generally refer to processor 60 (or another processor) receiving a bioelectrical brain signal, this may indicate that processor 60 (or another processor) receives information representative of the bioelectrical brain signal. The information representative of the bioelectrical brain signal may be, for example, a raw bioelectrical brain signal sensed by sensing module 66 of IMD 16 (or another sensing module), a parameterized bioelectrical brain signal generated by sensing module 66 or data generated based on the raw bioelectrical brain signal, such as one or more signal characteristics extracted from the sensed bioelectrical brain signal.

In addition or instead of automatically receiving sensed bioelectrical brain signals from sensor 66, in some examples, processor 60 is configured to receive the bioelectrical brain signal sensed by sensing module 66 in response to user input initiating a bioelectrical brain signal sensing. Processor 60 may receive the user input, for example, via IMD 16 or via programmer 14. For example, a motion sensor (e.g., an accelerometer, pressure transducer, gyroscope, or piezoelectric crystal) integrated into or on housing 34 of IMD 16 may be configured to generate a signal that is indicative of patient 12 tapping IMD 14 through the skin. The number, rate, or pattern of taps may be associated with the different stimulation therapies, and 60 may identify the tapping by patient 12 to determine when patient input is received. As another example, patient 12 may interact with user interface 86 of programmer 14 to provide input, and processor 80 of programmer 14 may transmit an indication of the receipt of the patient input to programmer 60 via the respective telemetry modules 84, 70.

In the technique shown in FIG. 4, processor 60 of IMD 16 determines whether the sensed bioelectrical brain signal includes a biomarker (102). In some cases, processor 60 determines the sensed bioelectrical brain signal includes the biomarker in response to determining the sensed bioelectrical brain signal includes a particular signal characteristic. In other examples, processor 60 determines the sensed bioelectrical brain signal includes the biomarker in response to determining a particular signal characteristic is absent from the sensed bioelectrical brain signal. In some examples, processor 60 substantially continuously receives (e.g., continuously receives or nearly continuously receives) the bioelectrical brain signal sensed by sensing module 66, but only samples the bioelectrical brain signal and determines whether the sampled bioelectrical brain signal includes a biomarker (102) at predetermined intervals, random (or pseudo-random) intervals, in response to user input, or any combination thereof (e.g., as described above with respect to receiving the bioelectrical brain signal). The frequency with which processor 60 samples the sensed bioelectrical brain signal or determines whether the sensed bioelectrical brain signal includes a biomarker may be selected by a clinician in some examples. In some examples, the frequency with which processor 60 samples the bioelectrical brain signal may be selected to be high enough such that the retrospective temporal bioelectrical brain signal history may be reconstructed based on the sample segments. This may be valuable temporal data that processor 80 of programmer 14 (or a processor of another device) may present to a user via user interface 86, e.g., as a graphical display, along with a date and time stamp. The temporal data may provide insight of the patient's response to certain sets of therapy parameter values.

In other examples of the technique shown in FIG. 4, in addition to or instead of generating a notification in response to determining a sensed bioelectrical brain signal includes a biomarker, processor 60 may generate a notification in response to determining the bioelectrical brain signal includes a biomarker, and patient 12 has experienced a threshold number or threshold frequency of episodes related to the patient condition for which IMD 16 is configured to manage. An episode may be, for example, the occurrence of a symptom related to the patient's condition, such as an aura related to a seizure, a seizure, a tremor related to a movement disorder, or a headache related to a chronic migraine or a cluster headache condition. The number or frequency of episodes may also indicate that the efficacy of therapy delivery by IMD 16 may have changed.

For example, patient 12 may provide input (e.g., via user interface 86 of programmer 14 or by tapping IMD 16) each time an episode (or event) is detected. In response to receiving the user input, processor 60 (or processor 80 of programmer 14) may generate an episode marker (which may also be referred to as an event marker in some examples). The episode marker may be, for example, a value, flag or signal that is stored by processor 60 within memory 62 (or a memory of another device). If processor 60 determines a sensed bioelectrical brain signal includes a biomarker, then processor may determine whether the number of episode markers (e.g., the gross number of stored episode markers or the number of episode markers within particular range of time) or the frequency of episodes (e.g., the number of episode markers generated within a particular range of time) is greater than or equal to an predetermined episode threshold. In response to determining the number of episode markers or the frequency of episodes is greater than or equal to a predetermined episode threshold and the sensed bioelectrical brain signal includes a biomarker, processor 60 may generate a notification (104).

Figure 5:
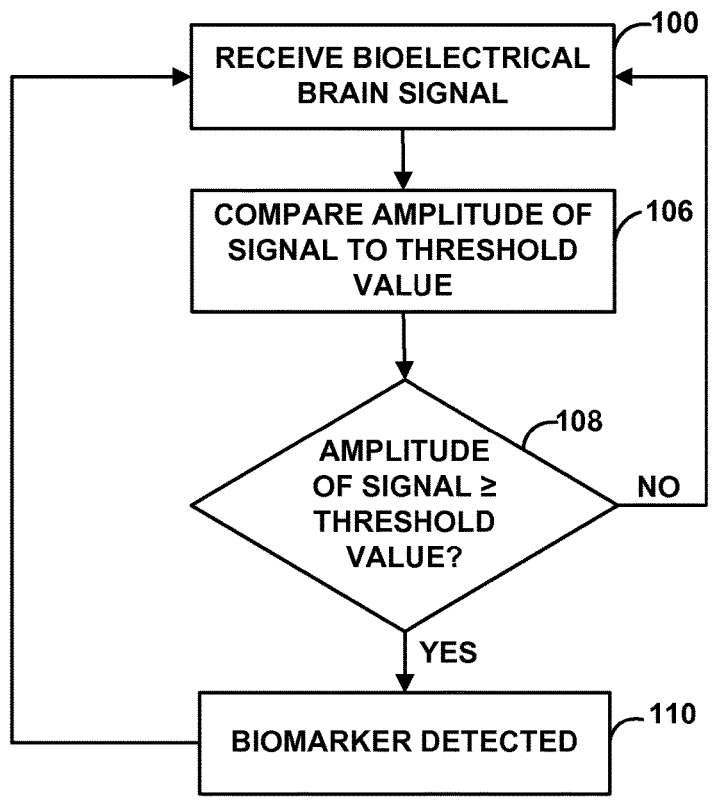
FIG. 5 is a flow diagram illustrating an example technique for determining whether a sensed bioelectrical brain signal includes a biomarker.
Figure 6:
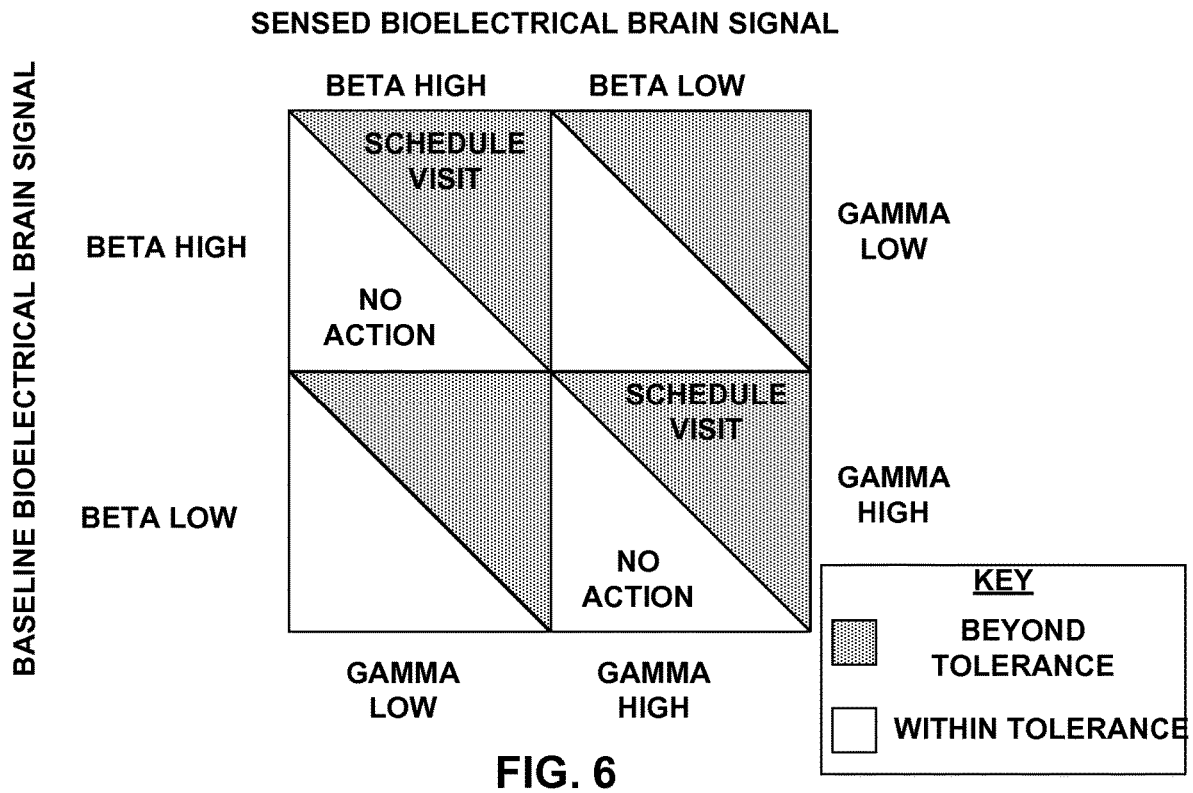
FIG. 6 is a table that illustrates example criteria for determining whether a bioelectrical brain signal indicates efficacy of one or more therapy parameters with which therapy is delivered to a patient may have changed.
Figure 8:
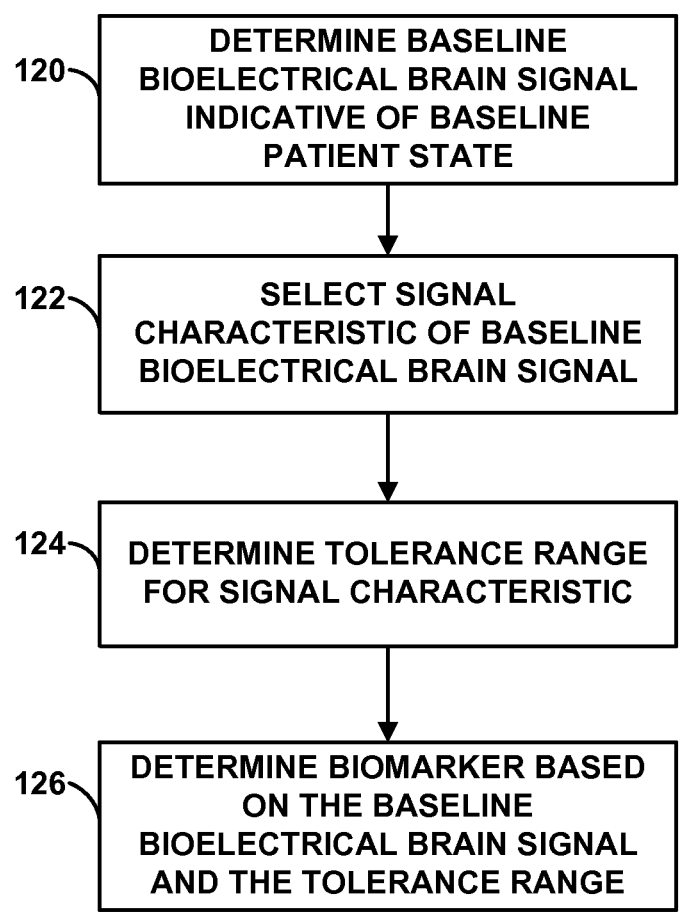
FIG. 8 is a flow diagram illustrating an example technique for determining a biomarker that indicates efficacy of one or more therapy parameters with which therapy is delivered to a patient may have changed.

As discussed above, processor 60 may determine whether a sensed bioelectrical brain signal includes a biomarker (102) using any suitable technique. FIGS. 5 and 6, described in further detail below, are flow diagrams illustrating example techniques that processor 60 may use to determine whether a sensed bioelectrical brain signal includes a biomarker (102). FIG. 8, described in further detail below, is a flow diagram illustrating an example technique that processor 60 may use to determine a biomarker indicative of a change in efficacy of therapy delivery, based on which processor 60 may initiate the generation of a notification.

In response to determining the sensed bioelectrical brain signal does not include the biomarker ("NO" branch of block 102), processor 60 may continue monitoring sensed bioelectrical brain signals for biomarkers. For example, processor 60 may continue receiving a bioelectrical brain signal (e.g., information representative of the bioelectrical brain signal) (100) and determining whether the bioelectrical brain signal includes a biomarker (102). Processor 60 may continue receiving the bioelectrical brain signal (100) at any suitable frequency, which may be regular or irregular, or based on user input (e.g., initiated by patient, patient caretaker, or clinician input).

In response to determining the sensed bioelectrical brain signal includes the biomarker ("YES" branch of block 102), processor 60 may generate a notification (e.g., to patient 12 or a patient caretaker) (104). Processor 60 may be configured to provide a notification using any suitable technique. In some examples, processor 60 may be configured to control programmer 14 to display a visible message, emit an audible alert signal or provide a somatosensory alert (e.g., by causing a housing of programmer 14 to vibrate in a particular pattern or to just vibrate continuously for a period of time) via user interface 86 in order to provide the notification, or any combination of the aforementioned types of notifications. In addition or instead of the notifications provided via programmer 14, the notifications may be provided via another external device or via IMD 16. For example, processor 60 may cause outer housing 34 (FIG. 1) of IMD 16 to provide a somatosensory alert (e.g., by causing housing 34 of IMD 16 to vibrate in a particular pattern or to just vibrate continuously for a period of time) in order to provide the notification.

In other examples, processor 60 may be configured to provide a notification by sending a signal, via telemetry module 70, to a remote device, from which a clinician or another user may receive the notification. The remote device may be communicatively linked to IMD 16 (or programmer 14) using any suitable system. An example of suitable system includes the CareLink Network, available from Medtronic, Inc. of Minneapolis, Minn., which may include n external device, such as a server, and one or more computing devices that are coupled to IMD 16 and programmer 14 via a network.

Processor 60 may employ one or more suitable signal processing techniques to determine whether a sensed bioelectrical brain signal has a biomarker indicative of a change in efficacy of electrical stimulation therapy delivered by IMD 16. FIG. 5 is a flow diagram illustrating an example technique for determining whether a sensed bioelectrical brain signal includes a biomarker based on a particular relationship of the voltage or current amplitude of the bioelectrical brain signal waveform to a threshold value.

In the technique shown in FIG. 5, processor 60 receives a bioelectrical brain signal (information representative of the bioelectrical brain signal) (100), and compares an amplitude of the bioelectrical brain signal to an amplitude threshold value (106). The amplitude may be, for example, any one or more of an absolute amplitude value or a root mean square amplitude value, an average, peak, median, or instantaneous amplitude value over a period of time or a maximum amplitude or an amplitude in a particular percentile of the maximum (e.g., an amplitude value that represents 95% of the maximum amplitude value of the segment of the sampled bioelectrical brain signal). The amplitude threshold value may be stored by memory 62 of IMD 16 (FIG. 2), memory 82 of programmer 14 (FIG. 3) or a memory of another device. A clinician may select the amplitude threshold value based on, for example, a baseline bioelectrical brain signal, as discussed in further detail with respect to FIG. 8.

In response to determining the amplitude of the bioelectrical brain signal is greater than or equal to the amplitude threshold value ("YES" branch of block 108), processor 60 determines that the biomarker is detected (110). In response to determining the amplitude of the bioelectrical brain signal is less than the threshold value ("NO" branch of block 108), processor 60 determines that the bioelectrical brain signal does not include the biomarker, and may continue monitoring received bioelectrical brain signals (100). Processor 60 may repeat the process shown in FIG. 5 until the biomarker is detected (110) in a sampled bioelectrical brain signal. In some examples, processor 60 performs the technique shown in FIG. 5 randomly or pseudo-randomly, according to a predetermined frequency or schedule, or in response to receiving user input (e.g. via IMD 16 or programmer 14).

In some examples, processor 60 may determine whether a sensed bioelectrical brain signal includes a biomarker indicative of a change in the efficacy of therapy delivery by IMD 16 based on a frequency band characteristic of the bioelectrical brain signal. Different frequency bands of a bioelectrical brain signal are associated with different activity in brain 28. One example of the frequency bands is shown in Table 1 below:

TABLE 1

| Frequency (f) Band Hertz (Hz) | Frequency Information |
|---|---|
| f < 5 Hz | δ (delta frequency band) |
| 5 Hz ≤ f ≤ 10 Hz | α (alpha frequency band) |
| 10 Hz ≤ f ≤ 30 Hz | β (beta frequency band) |
| 50 Hz ≤ f ≤ 100 Hz | γ (gamma frequency band) |
| 100 Hz ≤ f ≤ 200 Hz | high γ (high gamma frequency band) |

Sensing module 66 or processor 60 of IMD 16 (or another device) may tune a sensed bioelectrical brain signal to a particular frequency band that may be indicative of the efficacy of therapy delivery. It is believed that some frequency bands of a bioelectrical brain signal may be more revealing of the patient state (e.g., for purposes of assessing the efficacy of therapy delivery) than other frequency bands. As a result, the one or more frequency bands that are indicative of the efficacy of therapy delivery may change depending on the patient condition. For example, in the case of Parkinson's disease, sensing module 66 or processor 60 may tune the bioelectrical brain signal to the beta and gamma bands.

FIG. 6 is a decision table that illustrates example signal characteristics that may indicate the efficacy of therapy delivery by IMD 16 in some examples in which IMD 16 delivers therapy to patient 12 to manage Parkinson's disease. The signal characteristics that may be revealing of the patient state with some patients with Parkinson's disease is the power level in the beta band and the power level in the gamma band of a bioelectrical brain signal, or, in some examples, the ratio of the beta band power level and the gamma band power level. The table shown in FIG. 6 illustrates the relationship between the power levels within the beta and gamma bands and the efficacy of therapy delivery by IMD 16.

As FIG. 6 illustrates, in some examples, a bioelectrical brain signal of a patient that is receiving efficacious electrical stimulation therapy to manage Parkinson's disease may have a relatively low beta band power and a relatively high gamma band power level. Thus, using the decision table shown in FIG. 6, if processor 60 determines a sensed bioelectrical brain signal (e.g., received from sensing module 66) has a relatively high beta band power, e.g., a beta band power level that is greater than the beta band power level of the baseline bioelectrical brain signal and outside the beta band tolerance range (measured relative to the beta band power level of the baseline bioelectrical brain signal), and a gamma band power level that is relatively low, e.g., less than the gamma band power level of the baseline bioelectrical brain signal and outside the gamma band tolerance range, processor 60 may determine that the efficacy of the patient state has changed. In response to determining the sensed bioelectrical brain signal meets this set of criteria, processor 60 may generate a notification or take another responsive action (e.g., modifying therapy delivery, as discussed with respect to FIGS. 9 and 10). A sensed bioelectrical brain signal that has a relatively high beta band power level and a relatively low gamma band power level may indicate the efficacy of therapy delivered by IMD 16 may have changed, such that assessment of the therapy programs implemented by IMD 16 may be desirable.

Figure 7:
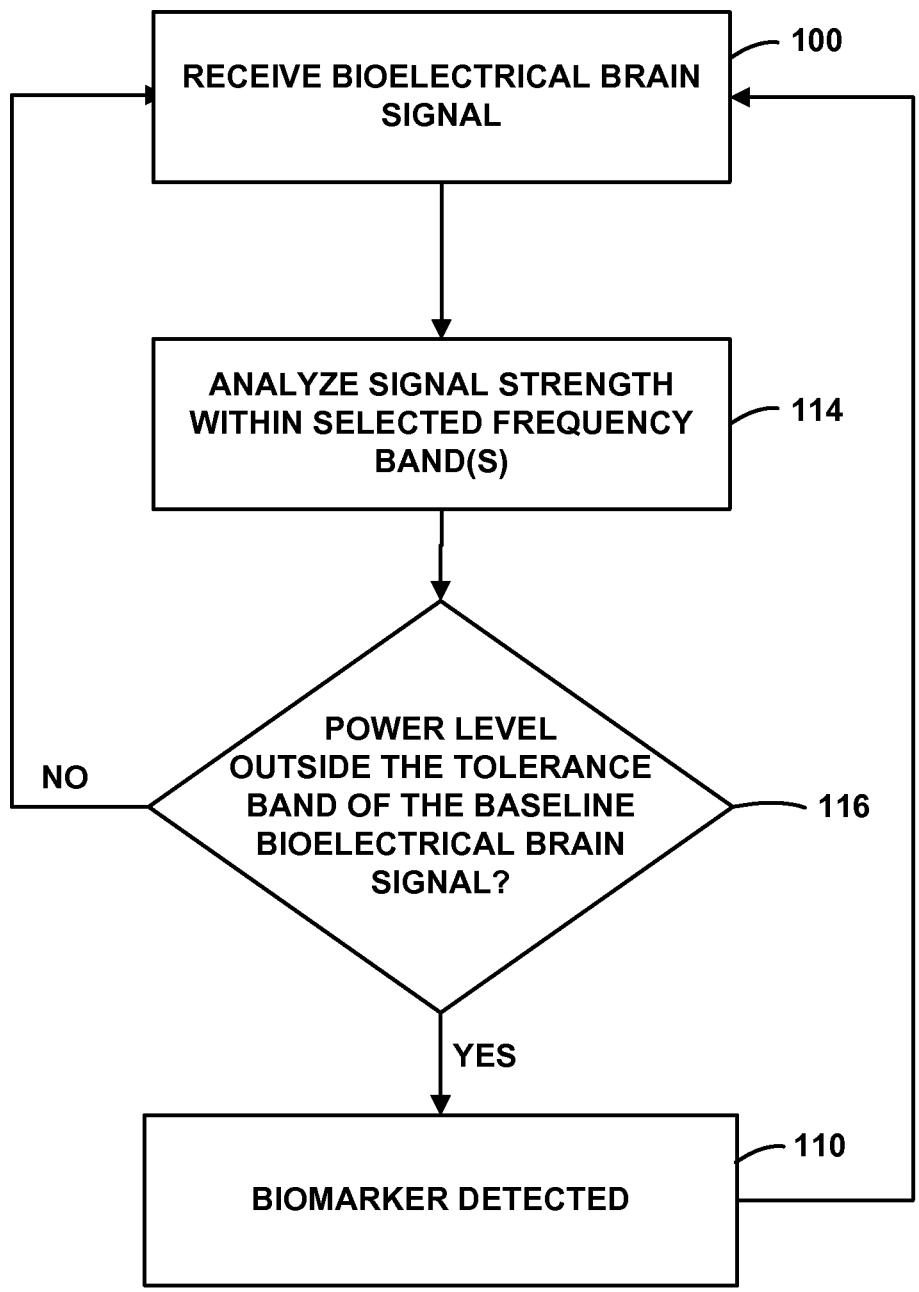
FIG. 7 is a flow diagram illustrating another example technique for determining whether a sensed bioelectrical brain signal includes a biomarker.

FIG. 7 is a flow diagram illustrating an example technique for determining whether a sensed bioelectrical brain signal includes a biomarker based on a frequency band characteristic of a sensed bioelectrical brain signal. In the technique shown in FIG. 7, processor 60 receives information representative of a bioelectrical brain signal (100), and, based on the received information, analyzes the signal strength of the bioelectrical brain signal within one or more selected frequency bands (114). A signal strength of the bioelectrical brain signal within a particular frequency band may also be referred to as the power level within the particular frequency band.

In the example shown in FIG. 7, processor 60 determines whether the power level within the one or more selected frequency bands is outside of a tolerance range of the power level of the one or more selected frequency bands of a baseline bioelectrical brain signal (116). In some examples, processor 60 compares power levels in different frequency bands or otherwise determines power levels in different frequency bands as a condition for the detection of the biomarker. In other examples, processor 60 may determine whether the biomarker is detected by determining whether the power level within the one or more selected frequency bands is within a tolerance range of the power level of the one or more selected frequency bands of a baseline bioelectrical brain signal.

As described in further detail below with respect to FIG. 8, the baseline bioelectrical brain signal may be a bioelectrical brain signal sensed when therapy delivery by IMD 16 was determined to be efficacious. Thus, one or more selected signal characteristics, e.g., the power level within one or more selected frequency bands, of the baseline bioelectrical brain signal may be indicative of a baseline patient state, and therapy delivery by IMD 16 may be implemented to achieve the baseline patient state. The tolerance range may represent the signal characteristics, relative to the baseline bioelectrical brain signal, that are still considered to be indicative of the baseline patient state. A clinician may select the tolerance range, e.g., as a percentage of the signal characteristic of the baseline bioelectrical brain signal, although the tolerance range can be defined using other techniques, such as a predefined numerical range. In the example shown in FIG. 7, the tolerance range is a definite range of power levels within the one or more selected frequency bands.

In response to determining the power level of the selected frequency band is outside of the tolerance range of the baseline bioelectrical brain signal ("YES" branch of block 116), processor 60 determines that the biomarker is detected (110). For example, if the selected frequency band is a beta band of the sensed bioelectrical brain signal, processor 60 may detect the biomarker in response to determining a sensed bioelectrical brain signal has a beta band power level that is greater than the beta band power level of a baseline bioelectrical brain signal and outside a tolerance range of the beta band power level of the baseline bioelectrical brain signal. The tolerance range may define, for example, how much greater a beta band power level of a sensed bioelectrical brain signal may be before the efficacy of the therapy delivered by IMD 16 is considered to have changed. In this example, processor 60 may detect the biomarker in response to determining a sensed bioelectrical brain signal has a beta band power level that is greater than the beta band power level and greater than the greatest beta band power level of the tolerance range. In this example, processor 60 may determine the biomarker is not present in response to determining the sensed bioelectrical brain signal has a beta band power level that is less the beta band power level of the baseline bioelectrical brain signal or greater than the beta band power level of the baseline bioelectrical brain signal and within of the tolerance range of the beta band power level of the baseline bioelectrical brain signal.

As indicated above, in some examples, processor 60 may detect a biomarker based on the power level in more than one frequency band of a sensed bioelectrical brain signal. For example, the selected frequency bands may be a beta band and a gamma band of the sensed bioelectrical brain signal. In these examples, processor 60 may detect the biomarker in response to determining a sensed bioelectrical brain signal has a beta band power level that is greater than the beta band power level of a baseline bioelectrical brain signal and outside a tolerance range of the beta band power level of the baseline bioelectrical brain signal, and a gamma band power level that is less than the gamma band power level of the baseline bioelectrical brain signal and outside a tolerance range of the gamma band power level of the baseline bioelectrical brain signal.

In response to determining the power level of the selected frequency band is within the tolerance range of the baseline bioelectrical brain signal ("NO" branch of block 116), processor 60 determines that the biomarker is not detected. Processor 60 may repeat the process shown in FIG. 7 until the biomarker is detected (110) in a sampled bioelectrical brain signal. In some examples, processor 60 performs the technique shown in FIG. 7 randomly or pseudo-randomly, at a predetermined frequency, according to a predetermined schedule, or in response to receiving user input.

FIG. 8 is a flow diagram illustrating an example technique for determining a biomarker indicative of a change in efficacy of therapy delivery by IMD 16. In the technique shown in FIG. 8, processor 60 determines a baseline bioelectrical brain signal indicative of a baseline patient state (120). As discussed above, the baseline patient state may be a state in which patient 12 is receiving efficacious therapy delivery by IMD 16. For example, the baseline patient state may be a state in which therapy delivery by IMD 16 is helping to reduce or even eliminate one or more symptoms of a patient condition for which therapy system 10 is implemented to manage. Thus, processor 60 may determine the baseline bioelectrical brain signal when therapy delivery by IMD 16 is known to be efficacious. In some examples, processor 60 may determine the baseline bioelectrical brain signal after the effects of the electrical stimulation therapy by IMD 16 have reached a relatively stable (or steady) state. In some cases, there may be a latency in response of patient 12 to the electrical stimulation therapy, and so it may be useful to wait some period of time (e.g., on the order of hours or even days) before determining the baseline bioelectrical brain signal indicative of a baseline patient state.

In some examples in which patient 12 is also taking medications (e.g., oral medications) or receiving another therapy in addition to electrical stimulation therapy delivered by IMD 16, processor 60 may determine the baseline bioelectrical brain signal when patient 12 is not taking the medication or receiving the other therapy. In other examples in which patient 12 is also taking medications or receiving another therapy, processor 60 may determine the baseline bioelectrical brain signal when patient 12 is taking the medication or receiving the other therapy.

Processor 60 may select a signal characteristic of a bioelectrical brain signal that is indicative of a particular patient state, where the signal characteristic changes as a function of the efficacy of therapy delivery by IMD 16 (e.g., changes as a function in the reduction of one or more patient symptoms) (122). The signal characteristic may be, for example, any one or more of a time domain characteristic of a bioelectrical brain signal (e.g., a mean, median, peak or lowest amplitude, instantaneous amplitude, pulse frequency or pulse to pulse variability), a frequency domain characteristic of a bioelectrical brain signal (e.g., a power level in one or more frequency bands or a ratio of power levels in two frequency bands), a pattern of the bioelectrical brain signal over time, or some other observable characteristic of a sensed bioelectrical brain signal.

Processor 60 may, in some examples, determine a tolerance range for the signal characteristic, where the tolerance range may define a range of values for the signal characteristic that are indicative of the baseline patient state (124). The tolerance range may be, for example, a permissible change in the value of the signal characteristic (e.g., a percentage) or a numerical range of values for the signal characteristic. In some examples, processor 60 determines the tolerance range based on input by a clinician (e.g., received via user interface 86 of programmer 14). The tolerance range may vary depending on one or more factors, such as the severity of the patient condition, the type of patient condition, patient preference, clinician preference, or any combination of these factors.

In some examples, the tolerance range may be selected based on the baseline bioelectrical brain signal and a bioelectrical brain signal sensed when patient 12 was known to be symptomatic. The tolerance range may be, for example, centered at or may begin at the baseline signal characteristic value (of the baseline bioelectrical brain signal) and may extend to the signal characteristic value that is midway between the baseline signal characteristic value and the value of the signal characteristic of the bioelectrical brain signal sensed when patient was known to be symptomatic. In this way, the tolerance range may be selected to define a permissible range of patient states between the baseline patient state and a state in which patient 12 was known to be symptomatic.

After processor 60 determines the tolerance range for the signal characteristic (124), processor 60 may determine the biomarker based on the baseline bioelectrical brain signal and the tolerance range (126), or, in some examples, based on only the tolerance range. If the tolerance range is a percentage or otherwise dependent on the value of the signal characteristic of the baseline bioelectrical brain signal, processor 60 may determine the biomarker based on the baseline bioelectrical brain signal and the tolerance range (126). On the other hand, if the tolerance range determined by processor 60 is a numerical range of values, processor 60 may determine the biomarker based on only the tolerance range (126).

In some examples, processor 60 may determine the biomarker to be any value of the signal characteristic that is outside of the tolerance range. The tolerance range corresponds to a baseline patient state in which the effects of therapy delivery by IMD 16 are efficacious. Thus, a sensed bioelectrical brain signal that has a signal characteristic with a value that is outside of the tolerance range may indicate that the effects of therapy delivery by IMD 16 may have changed relative to the baseline patient state.

In other some examples, processor 60 may determine the biomarker to be any value of the signal characteristic that is greater than the greatest value of the tolerance range. In yet other examples, processor 60 may determine the biomarker to be any value of the signal characteristic that is less than the lowest value of the tolerance range. The selection of the biomarker may depend on both the patient condition and the type of signal characteristic on which the biomarker is determined.

FIG. 9 is a flow diagram of another example technique for generating a notification that indicates efficacy of therapy delivery by IMD 16 may have changed. Again, while FIG. 9 and many of the other figures are described with respect to processor 60 of IMD 16, in other examples, a processor of another device (e.g., programmer 14) may perform the technique shown in FIG. 9 or any of the other techniques described herein. In the technique shown in FIG. 9, processor 60 is configured to determine whether the confidence level of a sensed bioelectrical brain signal meets a certain threshold (e.g., a predetermined threshold) before generating a notification based on the sensed bioelectrical brain signal. Determining whether the confidence level of a sensed bioelectrical brain signal meets a threshold may help ensure processor 60 is evaluating the efficacy of therapy delivery by IMD 16 based on a reliable and informative bioelectrical brain signal.

After processor 60 receives information representative of a sensed bioelectrical brain signal (100), e.g., from sensing module 66 of IMD 16 (FIG. 2), processor 60 determines whether the confidence in the sensed bioelectrical brain signal is greater than or equal to a confidence threshold (128). The confidence threshold may be, for example, selected to be a signal strength of a bioelectrical brain signal that reliably indicates the physiological activity of brain 28 of patient 12. For example, the confidence threshold may be selected to be a signal strength of a bioelectrical brain signal that has a relatively low background noise level.

Processor 60 may determine whether the confidence of a sensed bioelectrical brain signal is greater than or equal to the confidence threshold (128) using any suitable technique.

In some examples, processor 60 may determine the confidence level in the sensed bioelectrical brain signal based on the consistency of the sensed bioelectrical signal. For example, processor 60 may determine the confidence of the sensed bioelectrical brain signal is greater than or equal to the confidence threshold by comparing a variability of the sensed bioelectrical brain signal to the confidence threshold, which may define a threshold variability indicative of a signal having a sufficiently high confidence. In response to determining the variability of the sensed bioelectrical brain signal is less than or equal to a predetermined threshold or within a tolerance range of the variability of a baseline bioelectrical brain signal, processor 60 may determine that the confidence in the sensed bioelectrical brain signal is greater than or equal to a confidence threshold ("YES" branch of block 128).

As another example, processor 60 may determine confidence level in the sensed bioelectrical brain signal based on a strength of the sensed bioelectrical brain signal, which may be measured as a function of the area under a squared signal curve or a root means square amplitude value calculated based on the sensed bioelectrical brain signal. In this example, the confidence threshold may be a strength level. In response to determining the strength of the sensed bioelectrical brain signal is greater than or equal to a threshold strength level, processor 60 may determine that the confidence in the sensed bioelectrical brain signal is greater than or equal to the confidence threshold ("YES" branch of block 128).

In another example, processor 60 may determine confidence level in the sensed bioelectrical brain signal based on the background noise level of the sensed bioelectrical brain signal (e.g., the signal-to-noise ratio). In response to determining the background noise level of the sensed bioelectrical brain signal is less than or equal to the threshold value, processor 60 may determine that the confidence in the sensed bioelectrical brain signal is greater than or equal to the confidence threshold ("YES" branch of block 128). Processor 60 may also, in some examples, use any combination of the consistency of the sensed bioelectrical signal, the strength of the sensed bioelectrical brain signal, and the background noise level of the sensed bioelectrical brain signal to determine whether the confidence in the sensed bioelectrical brain signal is greater than or equal to the confidence threshold (128). Processor 60 may use another technique or combination of techniques in addition to or instead of the techniques described above to determine whether the confidence in the sensed bioelectrical brain signal is greater than or equal to the confidence threshold (128).

In some examples, in response to determining the confidence level is greater than or equal to the confidence threshold ("YES" branch of block 128), processor 60 may determine whether the sensed bioelectrical brain signal includes the biomarker associated with the notification (102), and generate the notification in response to determining the bioelectrical brain signal includes the biomarker associated with the notification (104). In other examples, processor 60 may generate the notification in response to determining a plurality of samples (e.g., continuous segments of the received bioelectrical brain signal) of the bioelectrical brain signal have a confidence level greater than or equal to the confidence threshold and also include the biomarker. This may help ensure processor 60 is responding to a relatively stable patient state in which the efficacy of therapy delivery by IMD 16 may have changed.

In the technique shown in FIG. 9, in response to determining the confidence level of a sample of the sensed bioelectrical brain signal is low ("NO" branch of block 128), processor 60 may increment a counter (130), and determine whether the counter is greater than or equal to a counter threshold (132). The counter can be implemented by software, hardware, firmware, or any combination thereof. For example, when processor 60 increments the counter, processor 60 may generate a flag, value or other indication generated by processor 60 and stored by memory 62 of IMD 16 or a memory of another device. As another example, the counter may be implemented by a register-type circuit and processor 60 may cause a state of the register-type circuit to change in order to increment or otherwise manage the counter. Counters having other configurations may also be used.

In response to determining the counter is less than the counter threshold ("NO" branch of block 132), processor 60 may sense another sample of a sensed bioelectrical brain signal (100) and determine whether the confidence in the sampled portion of the bioelectrical brain signal is greater than or equal to a confidence threshold (128). For example, processor 60 may control sensing module 66 of IMD 16 (or a separate sensing module) to sense a bioelectrical brain signal at a subsequent time and determine the confidence level in the subsequently sensed bioelectrical brain signal (128). For example, processor 60 may control sensing module 66 to sense a bioelectrical brain signal at randomly or pseudo-randomly selected times, predetermined intervals or in response to user input. Processor 60 may repeat this sampling of the bioelectrical brain signal until a bioelectrical brain signal meeting the confidence threshold is received or until a threshold number of sense attempts have been reached, as indicated by the value of the counter being greater than or equal to the counter threshold ("YES" branch of block 132). Processor 60 may increment the counter for each sample. In this way, processor 60 may attempt to find a bioelectrical brain signal having a relatively high confidence level prior to determining whether a biomarker is present in a sensed bioelectrical brain signal.

In some examples, processor 60 may only increment the counter (130) for each consecutive sample of the bioelectrical brain signal that does not meet the confidence threshold. In these examples, processor 60 may reset the counter to zero each time a received bioelectrical brain signal having a relatively high confidence level is detected. In other examples, processor 60 may increment the counter for nonconsecutive bioelectrical brain signal samples that do not meet the confidence threshold, and reset the counter at other times, e.g., if bioelectrical brain signals meeting the confidence threshold are detected one immediately after the other, or after a predetermined period of time.

In response to determining the counter is greater than or equal to the counter threshold ("YES" branch of block 132), processor 60 may take one or more responsive actions. In the example shown in FIG. 9, processor 60 controls stimulation generator 64 (or another therapy module if IMD 16 is configured to deliver another type of therapy) to revert to a known safe mode (134). Processor 60 may also generate a notification to the patient (or patient caretaker) that a visit to the clinician is recommended (134). In some examples, processor 60 controls stimulation generator 64 to revert to a safe mode by controlling stimulation generator to generate and deliver electrical stimulation therapy to patient 12 according to a set of stimulation parameter values that is known to provide a safe and comfortable therapy to patient 12. In some examples, the stimulation parameter values of the safe mode to may be selected to help ensure patient 12 is given a certain minimum amount of stimulation therapy (e.g., in an open-loop manner). The safe mode may be customizable and may be device, clinician, therapy and/or patient specific. The safe mode settings (e.g., stimulation parameter values) may be selected by a clinician in some examples, and may depend upon the patient needs and/or the type of therapy delivered by IMD 16.

In some examples, in the known safe mode, IMD 16 may stop delivering therapy to patient 12 or may revert to last known therapy parameters that yielded acceptable results. For example, the stimulation amplitude with which stimulation generator 64 generates and delivers electrical stimulation may be set to zero volts (or as close to zero volts as possible with the given hardware) in a safe mode. This may effectively turn off the stimulation and help remove any undesirable side effects of the therapy. For some therapies and patients, however, turning off the therapy may not be safe or comfortable. In other examples, stimulation generator 64 may generate and deliver electrical stimulation to patient 12 in the safe mode, and the therapy parameter values may be selected to yield a safe and comfortable level of stimulation for patient 12. In some examples, the safe mode is a preconfigured setting or a rollback to a last or last-known safe and comfortable therapy state.

In some examples, in addition to or instead of controlling stimulation generator 64 to revert to a safe mode and generating a notification, processor 60 may also store the sensed bioelectrical brain signals in memory 62 of IMD 16 or another device (e.g., programmer 14) for later retrieval and analysis by a clinician.

Processor 60 may implement another technique to improve the reliability of the biomarker detection instead of or in addition to determining whether a bioelectrical brain signal that has a relatively high confidence level includes the biomarker (e.g., as described with respect to FIG. 9). In some examples, processor 60 may determine whether a plurality of bioelectrical brain signals, where each signal is measured at a respective time (e.g., at five random times over a period of three to five days), exhibit a threshold level of accuracy and coherence. In this example, processor 60 may only determine whether a sensed bioelectrical brain signal includes the biomarker if the plurality of bioelectrical brain signals exhibit the threshold level of accuracy and coherence.

In some examples, IMD 16 is configured to deliver electrical stimulation therapy to patient 12 in a closed loop manner based on a bioelectrical brain signal. FIG. 10 is a flow diagram illustrating an example technique for adjusting therapy delivery by a medical device based on a sensed bioelectrical brain signal. In the example shown in FIG. 10, processor 60 modifies at least one therapy parameter value with which IMD 16 generates and delivers therapy to patient 12 in response to detecting a bioelectrical brain signal that includes a biomarker and prior to generating a notification. Modifying at least one therapy parameter value that defines the electrical stimulation therapy provided by IMD 16 may help change the efficacy of the therapy delivery by IMD 16, e.g., may help improve the efficacy of therapy indicated by the presence of the biomarker. In some examples, processor 60 may only control therapy delivery by IMD 16 in a closed-loop or pseudo-closed-loop manner, e.g., using the technique shown in FIG. 10, if the confidence level in the sensed bioelectrical brain signal is sufficiently high, as described above with respect to FIG. 9.

In the technique shown in FIG. 10, processor 60 receives information representative of a bioelectrical brain signal (100) and determines, based on the received information, whether the bioelectrical brain signal includes a biomarker (102). As discussed above, the received information representative of the bioelectrical brain signal may be, for example, a raw bioelectrical brain signal sensed by sensing module 66 of IMD 16 (or another sensing module), a parameterized bioelectrical brain signal generated by sensing module 66 or data generated based on the raw bioelectrical brain signal, such as one or more signal characteristics extracted from the sensed bioelectrical brain signal.

As discussed above with respect to FIG. 4, sensing module 66 of IMD 16 may sense the bioelectrical brain signal of patient 12 at randomly or pseudo-randomly selected times, according to a predetermined schedule, at predetermined intervals, in response to patient input, or substantially continuously. Processor 60 may, therefore, receive the information representative of a sensed bioelectrical brain signal (100) periodically or substantially continuously. In examples in which processor 60 receives the information representative of the sensed bioelectrical brain signal (100) substantially continuously, processor 60 may select a sample of the information (e.g., a sample of the received bioelectrical brain signal), such as a segment of the information representative of a bioelectrical brain signal having a particular duration of time, and determine whether the selected sample includes the biomarker (102). In examples in which processor 60 receives the sensed bioelectrical brain signal periodically, processor 60 may determine whether the received bioelectrical brain signal, which may be a segment of a bioelectrical brain signal having a particular duration of time, includes the biomarker (102).

In response to determining the sensed bioelectrical brain signal does not include the biomarker ("NO" branch of block 102), processor 60 may continue receiving a bioelectrical brain signal (100) and determining whether the bioelectrical brain signal includes a biomarker (102) until a bioelectrical brain signal includes the biomarker ("YES" branch of block 102).

In response to determining the sensed bioelectrical brain signal includes the biomarker ("YES" branch of block 102), processor 60 may modify at least one therapy parameter value with which IMD 16 generates and delivers therapy to patient 12 (138). In the example shown in FIG. 10, processor 60 may modify at least one stimulation parameter value with which stimulation generator 64 generates and delivers electrical stimulation therapy to patient 12. Processor 60 may modify at least one therapy parameter value (138), for example, modifying at least one therapy parameter value of a therapy program currently implemented by IMD 16 (and implemented by IMD 16 at the time the bioelectrical brain signal including the biomarker was sensed) or by selecting a different therapy program 74 from memory 62 (FIG. 2).

In some examples, memory 62 of IMD 16 or a memory of another device stores a plurality of therapy programs in a predetermined order, and processor 60 may modify at least one therapy parameter value (138) by at least selecting the next therapy program in the order (ranked after the currently implemented therapy program). A plurality of therapy programs 74 may be ordered (e.g., ranked), for example, based on any one or more factors, such as, but not limited to, the efficacy of therapy delivery (e.g., as indicated by patient input or based on a sensed physiological parameter of patient 12), a severity of side effects from therapy delivery according to the therapy programs, electrical efficiency of the therapy programs (e.g., defined by the amount power source 72 is drained during the generation and delivery of therapy according to a particular therapy program), and a size of a therapeutic window, which may be the difference in amplitude of the electrical stimulation signal between beneficial therapeutic effects and non-beneficial side-effects. The therapeutic window may indicate the amount a clinician may modify a therapy parameter value to manage disease progression in a given patient.

In addition, or instead, of the techniques described above, processor 60 may modify at least one therapy parameter value (138) using a genetic algorithm-based technique, such as the one described in commonly-assigned U.S. Pat. No. 7,239,926 to Goetz, entitled, "SELECTION OF NEUROSTIMULATION PARAMETER CONFIGURATIONS USING GENETIC ALGORITHMS," which issued on Jul. 3, 2007, and is incorporated herein by reference in its entirety. In one example described in U.S. Pat. No. 7,239,926 to Goetz, genetic algorithms provide guidance in the selection of stimulation parameters by suggesting the parameters that are most likely to be efficacious given the results of tests already performed during an evaluation session. Genetic algorithms encode potential solutions to a problem as members of a population of solutions. This population is then judged based on a fitness function. The best therapy programs are then retained and a new generation is created based upon their characteristics. The new generation is composed of solutions similar in nature to the best performers of the previous generation.

In addition, or instead, of the techniques described above, processor 60 may automatically modify at least one therapy parameter value (138) by implementing a methodical system of identifying potentially beneficial therapy parameter values for patient 12. In one example, processor 60 may implement a tree-based technique for selecting the therapy program. A programming tree structure may include a plurality of levels that are associated with a different therapy parameter. The tree may include nodes that are connected to nodes of adjacent levels, whereby each node defines values for at least one therapy parameter.

Examples of tree-based techniques that processor 60 may implement to modify at least one therapy parameter value (138), e.g., by modifying a therapy program or generating a new therapy program, are described in commonly-assigned U.S. Pat. No. 7,801,619 to Gerber et al., entitled, "TREE-BASED ELECTRICAL STIMULATION PROGRAMMING FOR PAIN THERAPY," which issued on Sep. 21, 2010; commonly-assigned U.S. Pat. No. 7,706,889 to Gerber et al., entitled, "TREE-BASED ELECTRICAL STIMULATOR PROGRAMMING," which issued on Apr. 27, 2010; commonly-assigned U.S. Pat. No. 7,715,920 to Rondoni et al., entitled, "TREE-BASED ELECTRICAL STIMULATOR PROGRAMMING," which issued on May 11, 2010; U.S. Pat. No. 7,617,002 to Goetz, entitled, "SELECTION OF NEUROSTIMULATOR PARAMETER CONFIGURATIONS USING DECISION TREES," which issued on Nov. 10, 2009; and U.S. Pat. No. 7,184,837 to Goetz, entitled, "SELECTION OF NEUROSTIMULATOR PARAMETER CONFIGURATIONS USING BAYESIAN NETWORKS," which issued on Feb. 27, 2007. The entire content of each of U.S. Pat. Nos. 7,801,619, 7,706,889, 7,715,920, 7,617,002, and 7,184,837 is incorporated herein by reference in its entirety.

In some examples, processor 60 modifies at least one therapy parameter value (138) by at least modifying the electrode combination (also referred to herein as a "stimulation electrode combination") with which IMD 16 delivers electrical stimulation signals to brain 28. Processor 60 may, for example, select a stimulation electrode combination (e.g., a subset of electrodes 24, 26 and the polarities of the subset) based on the frequency domain characteristics of one or more bioelectrical brain signals sensed with respective sense electrode combinations. In some examples, processor 60 may, for example, select an electrode combination (e.g., a subset of electrodes 24, 26 and the polarities of the subset) based on the electrodes that are determined to be closest to a target tissue site in brain 28, which may be determined based on the frequency domain characteristics of one or more bioelectrical brain signals sensed with respective sense electrode combinations.

In some examples, the sense electrodes (e.g., a subset of electrodes 24, 26) closest to a highest relative beta band activity within brain 28 may be mapped to a stimulation electrode combination that may provide relatively efficacious stimulation therapy. For example, the sense electrode combinations and the stimulation electrode combinations may be related by a functional relationship between different regions of brain 28. For example, a group of sense electrodes that senses a bioelectrical signal having a relatively high beta band power within a first part of the thalamus or sub-thalamus of brain 28 may be mapped to a second part of the thalamus or sub-thalamus that is functionally connected to the first part. This functional relationship may indicate that if electrical stimulation is delivered to the second part of the thalamus or sub-thalamus via a particular stimulation electrode combination, any irregular oscillations or other irregular brain activity within the first part of the thalamus or sub-thalamus may be effectively suppressed.

One example technique processor 60 may implement to select a stimulation electrode combination is selected based on a sense electrode combination determined to be closest to the target tissue site is described in U.S. Patent Application Publication No. 2010/0100153 by Carlson et al., entitled "STIMULATION ELECTRODE SELECTION," which published on Apr. 22, 2010 and is incorporated herein by reference in its entirety. U.S. patent application Ser. No. 12/563,845 by Carlson et al. describes, in some examples, techniques in which beta band power levels are recorded, analyzed, and compared to one another, and in which the sense electrode with the highest beta band power level is selected as the sense electrode closest to the target tissue site.

Other techniques that processor 60 may implement to select a stimulation electrode combination based on bioelectrical signals sensed within the patient's brain are described in U.S. Patent Application Publication No. 2011/0144715 by Molnar et al., entitled, "STIMULATION ELECTRODE SELECTION," which published on Jun. 16, 2011, and U.S. Patent Application Publication No. 2011/0144521 by Molnar et al., entitled, "STIMULATION ELECTRODE SELECTION," which published on Jun. 16, 2011. The entire content of U.S. Patent Application Publication No. 2011/0144715 by Molnar et al. and U.S. Patent Application Publication No. 2011/0144521 by Molnar et al. is incorporated herein by reference.

Some techniques described by U.S. Patent Application Publication No. 2011/0144715 by Molnar et al. and U.S. Patent Application Publication No. 2011/0144521 by Molnar et al. include selecting a stimulation electrode combination based on the one or more electrodes used to sense the bioelectrical brain signal that has the relatively highest energy level within a particular frequency band (e.g., a beta band, a gamma band, or both). The techniques described in U.S. Patent Application Publication No. 2011/0144715 by Molnar et al. and U.S. Patent Application Publication No. 2011/0144521 by Molnar et al. may facilitate determining the sense electrode or electrodes closest to a target tissue site, including in cases in which the target tissue site is between two sense electrodes.

In some examples, memory 62 of IMD 16 or another device may store a plurality of predetermined electrode combinations, which may be ordered in the memory based on the beta band activity, the gamma band activity, both or a ratio of both, evoked by the delivery of electrical stimulation according to the predetermined stimulation electrode combination. In order to compare the stimulation electrode combinations with each other, processor 60 may control IMD 16 to deliver test electrical stimulation to brain 28 of patient 12 with a common set of therapy parameter values (e.g., the pulse width and frequency) that define the stimulation signal, and a selected stimulation electrode combination (e.g. monopolar or unipolar and bipolar etc). In one example, the common set of therapy parameter values include a pulse width of about 60 microseconds and a frequency of about 130 Hertz (Hz).

Sensing module 66 may sense a bioelectrical brain signal after initiation of therapy delivery via a respective electrode combination, and processor 60 may determine the resulting beta band activity, gamma band activity, or both, of the sensed bioelectrical brain signal. The resulting beta band activity, gamma band activity, or both, of the sensed bioelectrical brain signal may indicate the efficacy of therapy via the respective stimulation electrode combination.

Processor 60 may test a plurality of electrode combinations in this manner, and store the electrode combinations in memory 62 along with the respective the beta band activity, the gamma band activity, or both. In some examples, processor 60 ranks the stimulation electrode combinations based on the beta band activity (e.g., the stimulation electrode combination that resulted in the relatively lowest beta band activity may be rank the highest for patients with Parkinson's disease), the gamma band activity (e.g., the stimulation electrode combination that resulted in the relatively highest gamma band activity may be rank the highest for patients with Parkinson's disease), or both (e.g., a ratio of gamma band to beta band activity or a difference between the beta band and gamma band power levels). At a later time, processor 60 may modify at least one therapy parameter value (138) by at least selecting a different stimulation electrode combination from memory 62.

In some examples, processor 60 modifies therapy program with which IMD 16 generates and delivers therapy to patient 12 only after determining a plurality of samples of the bioelectrical brain signal (e.g., continuous segments of a received bioelectrical brain signal or a plurality of bioelectrical brain signal segments received consecutively) include the biomarker. In this way, processor 60 may verify that the therapy delivery according to the currently implemented therapy parameter values (e.g., one or more therapy programs) may need to be modified based on a larger sample of bioelectrical brain signals than just one sample. This may also help ensure processor 60 is responding to a relatively stable patient state in which the efficacy of therapy delivery by IMD 16 may have changed.

Prior to or after modifying the at least therapy parameter value (138), processor 60 may increment a counter (140). The counter may be any suitable counter, such as the example counters described with respect to FIG. 9. The value of the counter represents the number of times processor 60 modified at least one therapy parameter value in response to detecting a bioelectrical brain signal including the biomarker.

After processor 60 modifies the at least one therapy parameter value (138), processor 60 may control stimulation generator 64 to generate and deliver electrical stimulation therapy to patient 12 according to the modified therapy (142), i.e., the therapy parameter values including the at least one modified therapy parameter value. For example, if processor 60 modified at least one therapy parameter value by changing the value of one type of therapy parameter of a therapy program that defines values for a plurality of types of therapy parameters, processor 60 may control stimulation generator 64 to generate and deliver electrical stimulation therapy to patient 12 according to the modified therapy program that includes the modified therapy parameter value and the therapy parameter values that were not modified.

In some examples, processor 60 determines whether the therapy delivery by IMD 16 according to the modified therapy parameter value was efficacious. In the example shown in FIG. 10, processor 60 determines whether the modified therapy was efficacious by at least determining whether a bioelectrical brain signal sensed after stimulation generator 64 initiated the delivery of electrical stimulation therapy to patient 12 according to the modified therapy includes the biomarker (144). The bioelectrical brain signal sensed after stimulation generator 64 initiated the delivery of electrical stimulation therapy to patient 12 according to the modified therapy may indicate the patient brain state evoked by the stimulation therapy defined by the modified therapy. In this way, the bioelectrical brain signal sensed after stimulation generator 64 initiated the delivery of electrical stimulation therapy to patient 12 according to the modified therapy may indicate whether the therapy delivery with the at least one modified therapy parameter value changed the efficacy of therapy delivery by IMD 16.

In response to determining the bioelectrical brain signal does not include the biomarker ("NO" branch of block 144), processor 60 may determine that the therapy delivery with the at least one modified therapy parameter value is efficacious (e.g., relative to a baseline patient state indicated by a baseline bioelectrical brain signal). Accordingly, in the technique shown in FIG. 10, in response to determining the bioelectrical brain signal does not include the biomarker ("NO" branch of block 144), processor 60 may continue controlling stimulation generator 64 to generate and deliver therapy according to the at least one modified therapy parameter value (142). If processor 60 does not detect the biomarker in a bioelectrical brain signal sensed after IMD 16 delivers therapy to patient 12 according to the modified therapy, then processor 60 may determine that a programming session with a clinician to improve the efficacy of therapy delivery by IMD 16 may not be recommended. Thus, in some examples, if processor 60 does not detect the biomarker in a bioelectrical brain signal sensed after IMD 16 delivers therapy to patient 12 according to the modified therapy, then processor 60 does not generate the notification.

In response to determining the bioelectrical brain signal includes the biomarker ("YES" branch of block 144), processor 60 may determine that the therapy delivery with the at least one modified therapy parameter value does not meet the threshold efficacy level (e.g., relative to a baseline patient state indicated by a baseline bioelectrical brain signal). In response to determining that the bioelectrical brain signal includes the biomarker ("YES" branch of block 144), processor 60 may determine whether the value of the counter is greater than or equal to a counter threshold (148). The value of the counter represents the number of times processor 60 modified at least one therapy parameter value in response to detecting a bioelectrical brain signal including the biomarker.

In the technique shown in FIG. 10, in response to determining the value of the counter is not greater than or equal to the counter threshold ("NO" branch of block 148), processor 60 modifies at least one therapy parameter value (138). This process may repeat until processor 60 determines the value of the counter is greater than or equal to the counter threshold ("YES" branch of block 148). In response to determining the value of the counter is greater than or equal to the counter threshold ("YES" branch of block 148), processor 60 may generate a notification (104), and, in some examples, control IMD 16 to revert to a safe mode (e.g., as described with respect to FIG. 9).

The counter threshold indicates the maximum number of iterations that processor 60 may modify at least one therapy parameter value (138). As a result, in response to determining the value of the counter is greater than or equal to the counter threshold, thereby indicating the therapy delivered by IMD 16 was modified a predetermined maximum number of times, processor 60 may determine that modification of the therapy delivery by IMD 16 was not successful in improving the efficacy of therapy delivery by IMD 16, such that a visit to the clinician is recommended. In the example shown in FIG. 10, the closed-loop therapy delivery by IMD 16 is also suspended by processor 60 in response to determining the value of the counter is greater than or equal to the counter threshold ("YES" branch of block 148). The counter threshold may, for example, be selected by a clinician in some examples.

Each time processor 60 modifies at least one therapy parameter value (138) in response to determining bioelectrical brain signal includes a biomarker (102, 144) may be referred to as an iteration of therapy modification. The at least one therapy parameter modified at each iteration of therapy modification may be the same or different than the therapy parameter modified during the previous iteration. In some examples, processor 60 may implement a plurality of rules for modifying the at least one therapy parameter value. The rules may specify, for example, the order in which the values of therapy parameters are modified (e.g., the order in which processor 60 modifies the current amplitude, voltage amplitude, frequency, and, in the case of stimulation pulses, pulse width of a stimulation signal generated and delivered by IMD 16) during a single iteration or between multiple iterations, whether processor 60 modifies the value of one therapy parameter at a time or a plurality of therapy parameter values over time, or any combination thereof.

In some examples, the time between iterations of therapy modification may be predetermined (e.g., by a clinician). Thus, in some examples, processor 60 is configured to modify at least one therapy parameter value (138) at a certain minimum frequency. This may help ensure that the effects of the therapy delivery according to the at least one modified therapy parameter value have reached a steady state before processor 60 determines whether the modified therapy is efficacious (e.g., based on whether a sensed bioelectrical brain signal includes a biomarker (144)).

In some examples, processor 60 restarts the counter each time a received bioelectrical brain signal does not include the biomarker (e.g., as described with respect to block 144). For example, processor 60 may restart the counter in response to determining a bioelectrical brain signal sensed after IMD 16 delivers therapy to patient 12 according to the modified therapy (with the at least one modified therapy parameter value) does not include the biomarker ("NO" branch of block 144). In other examples, processor 60 restarts the counter at predetermined intervals. This may help limit the frequency with which processor 60 may modify at least one therapy parameter value with which IMD 16 generates and delivers therapy to patient.

In the technique shown in FIG. 10, in response to determining the value of the counter is greater than or equal to the counter threshold ("YES" branch of block 148), processor 60 may cause a notification to be generated (104), e.g., using any of the techniques described above.

While the techniques described above are primarily described as being performed by processor 60 of IMD 16, in other examples, one or more other processors may perform any part of the techniques described herein alone or in addition to processor 60. Thus, reference to "a processor" may refer to "one or more processors." Likewise, "one or more processors" may refer to a single processor or multiple processors in different examples. For example, while in some examples described above, processor 60 generates a notification (104) in response to determining a bioelectrical brain signal includes a biomarker that indicates efficacy of therapy delivered by a medical device to the patient may have changed, in other examples, a processor of another device, e.g., processor 80 of programmer 14, may generate the notification (104). For example, in some examples, processor 60 of IMD 16 may receive the bioelectrical brain signal from sensing module 66 and transmit the bioelectrical brain signal (or other information representative of the signal) to processor 80 of programmer 14 (e.g., via the respective telemetry modules). Processor 80 may then generate the notification based on determining the bioelectrical brain signal includes the biomarker that indicates efficacy of therapy delivered by a medical device to the patient may have changed. In this example, processor 80 receives information representative of a sensed bioelectrical from IMD 16.

As another example, in some examples, processor 60 of IMD 16 may receive the bioelectrical brain signal from sensing module 66 and determine the bioelectrical brain signal includes the biomarker. Processor 60 may then transmit an indication (e.g., a signal) to processor 80 of programmer 14 that indicates the biomarker was detected and, in response to receiving the indication, processor 80 of programmer 14 may generate the notification. For example, processor 60 may transmit control signal processor 80 of programmer 14 that causes processor 80 to generate the notification. In this example, the indication transmitted by processor 60 of IMD 16 to processor 80 may be the information representative of a sensed bioelectrical.

The techniques described in this disclosure, including those attributed to IMD 16, programmer 14, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples have been described. These and other examples are within the scope of the following claims.

What is claimed is:

1. A method comprising:
controlling, with one or more processors, a medical device to deliver therapy to a patient according to a therapy program;
selecting, with the one or more processors, a biomarker stored in a memory, wherein the biomarker indicates a response of the patient to the therapy delivered by the medical device according to the therapy program may have changed relative to a response of the patient to the therapy delivered by the medical device according to the therapy program when the patient was in a baseline state in which efficacious therapy delivery by the medical device according to the therapy program was observed;
receiving, with the one or more processors, information representative of a bioelectrical brain signal of the patient;
determining, with the one or more processors, the bioelectrical brain signal includes the biomarker;
generating, with the one or more processors, a notification based on determining the bioelectrical brain signal includes the biomarker; and
controlling therapy delivery by the medical device based on determining the bioelectrical brain signal includes the biomarker; and
controlling therapy delivery by the medical device based on determining the bioelectrical brain signal includes the biomarker.

2. The method of claim 1, wherein receiving the information representative of the bioelectrical brain signal comprises receiving, with the one or more processors, the bioelectrical brain signal from a sensing module at periodic, predetermined, or random intervals.

3. The method of claim 1, wherein receiving the information representative of the bioelectrical brain signal comprises:
receiving, with the one or more processors, user input; and
receiving, with the one or more processors, the bioelectrical brain signal from a sensing module in response to receiving the user input.

4. The method of claim 1, wherein determining the bioelectrical brain signal includes the biomarker comprises comparing an amplitude of the bioelectrical brain signal to a threshold value.

5. The method of claim 1, wherein the bioelectrical brain signal comprises a sensed bioelectrical brain signal, and wherein determining the sensed bioelectrical brain signal includes the biomarker comprises comparing the sensed bioelectrical brain signal to a baseline bioelectrical brain signal.

6. The method of claim 1, wherein determining the bioelectrical brain signal includes the biomarker comprises comparing a first signal strength in at least one frequency band of the bioelectrical brain signal to a second signal strength in the at least one frequency band of a baseline bioelectrical brain signal.

7. The method of claim 1, wherein the bioelectrical brain signal comprises a sensed bioelectrical brain signal, and wherein determining the bioelectrical brain signal includes the biomarker comprises:
comparing a first power level in a beta band of the sensed bioelectrical brain signal with a second power level in the beta band of a baseline bioelectrical brain signal; and
comparing a third power level in a gamma band of the sensed bioelectrical brain signal with a fourth power level in the gamma band of the baseline bioelectrical brain signal,
wherein generating the notification comprises generating the notification in response to determining the first power level in the beta band of the sensed bioelectrical brain signal is greater than the second power level in the beta band of the baseline bioelectrical brain signal and the third power level in the gamma band of the sensed bioelectrical brain signal is less than the fourth power level in the gamma band of the baseline bioelectrical brain signal.

8. The method of claim 1, wherein generating the notification comprises generating at least one of a visible message, an audible signal or a somatosensory notification.

9. The method of claim 1, further comprising, prior to generating the notification, determining whether a confidence in the bioelectrical brain signal is greater than or equal to a confidence threshold, wherein determining the bioelectrical brain signal includes the biomarker comprises determining the bioelectrical brain signal includes the biomarker in response to determining the confidence in the bioelectrical brain signal is greater than or equal to the confidence threshold.

10. The method of claim 9, wherein determining whether the confidence in the bioelectrical brain signal is greater than or equal to the confidence threshold comprises comparing at least one of a consistency of the bioelectrical brain signal, a signal strength of the bioelectrical brain signal, or a background noise level of the bioelectrical brain signal to a predetermined threshold value.

11. The method of claim 9, wherein the bioelectrical brain signal comprises a first bioelectrical brain signal and the confidence comprises a first confidence, the method further comprising:
in response to determining the first confidence in the first bioelectrical brain signal is not greater than or equal to the confidence threshold, incrementing a counter;
after incrementing the counter, determining whether a value of the counter is greater than or equal to a counter threshold;

in response to determining the value of the counter is less than the counter threshold, determining whether a second confidence in a second bioelectrical brain signal sensed after the first bioelectrical brain signal is greater than or equal to the confidence threshold; and in response to determining the value of the counter is greater than or equal to the counter threshold, at least one of controlling the medical device to revert to a safe mode or generating the notification.

12. The method of claim 1, further comprising:
receiving a baseline bioelectrical brain signal;
selecting a signal characteristic of the baseline bioelectrical brain signal;
determining a tolerance range for the signal characteristic that indicates the baseline state; and
determining the biomarker based on the signal characteristic of the baseline bioelectrical brain signal and the tolerance range.

13. The method of claim 1, wherein the bioelectrical brain signal comprises a first bioelectrical brain signal, wherein controlling therapy delivery by the medical device based on determining the bioelectrical brain signal includes the biomarker comprises:
prior to generating the notification and in response to determining the first bioelectrical brain signal includes the biomarker, modifying the therapy program, wherein modifying the therapy program generates a modified therapy program;
controlling the medical device to deliver therapy to the patient according to the modified therapy program; and
determining, with the one or more processors, a second bioelectrical brain signal sensed after the medical device delivered the therapy to the patient according to the modified therapy program includes the biomarker, wherein the method further comprises generating a notification in response to determining the second bioelectrical brain signal includes the biomarker.

14. The method of claim 13, wherein modifying the therapy delivered by the medical device comprises modifying at least one therapy parameter value with which the medical device generates and delivers therapy to the patient.

15. The method of claim 1, wherein the bioelectrical brain signal comprises a first bioelectrical brain signal, wherein controlling therapy delivery by the medical device based on determining the bioelectrical brain signal includes the biomarker comprises:
prior to generating the notification and in response to determining the first bioelectrical brain signal includes the biomarker, modifying the therapy program, wherein modifying the therapy program generates a modified therapy program;
prior to or after modifying the therapy, incrementing a counter that indicates a number of therapy modification attempts;
controlling the medical device to deliver therapy to the patient according to the modified therapy program;
determining, with the one or more processors, a second bioelectrical brain signal sensed after the medical device delivered the therapy to the patient according to the modified therapy program includes the biomarker;
in response to determining the second bioelectrical brain signal includes the biomarker, determining whether a value of the counter is greater than or equal to a counter threshold;
in response to determining the value of the counter is less than the counter threshold, modifying the modified therapy program; and in response to determining the value of the counter is greater than or equal to the counter threshold, at least one of controlling the medical device to revert to a safe mode or generating the notification.

16. The method of claim 1, further comprising determining at least one of a number of episodes or a frequency of episodes experienced by the patient, wherein generating the notification comprises generating the notification in response to determining the bioelectrical brain signal includes the biomarker and the at least one of the number of episodes or the frequency of episodes experienced by the patient is greater than or equal to an episode threshold.

17. A system comprising:
a therapy module configured to deliver therapy to a patient according to a therapy program;
a memory storing a biomarker that indicates a response of the patient to the therapy delivered by the therapy module according to the therapy program may have changed relative to a response of the patient to the therapy delivered by the therapy module according to the therapy program when the patient was in a baseline state in which efficacious therapy delivery by the therapy module according to the therapy program was observed,
a sensing module configured to sense a bioelectrical brain signal of the patient; and
one or more processors configured to:
control the therapy module to deliver the therapy to the patient according to the therapy program,
select the biomarker stored in the memory,
determine the bioelectrical brain signal includes the biomarker,
generate a notification based on determining the bioelectrical brain signal includes the biomarker, and
control the therapy delivery by the therapy module based on determining the bioelectrical brain signal includes the biomarker.

18. The system of claim 17, wherein the one or more processors are configured to receive information representative of the bioelectrical brain signal from the sensing module at periodic, predetermined, or random intervals.

19. The system of claim 17, further comprising a user interface, wherein the one or more processors are configured to receive information representative of the bioelectrical brain signal from a sensing module in response to receiving user input via the user interface.

20. The system of claim 17, wherein the one or more processors are configured to determine the bioelectrical brain signal includes the biomarker by at least comparing an amplitude of the bioelectrical brain signal to a threshold value.

21. The system of claim 17, wherein the bioelectrical brain signal comprises a sensed bioelectrical brain signal, and wherein the one or more processors are configured to determine the sensed bioelectrical brain signal includes the biomarker by at least comparing the sensed bioelectrical brain signal to a baseline bioelectrical brain signal.

22. The system of claim 17, wherein the one or more processors are configured to determine the bioelectrical brain signal includes the biomarker by at least comparing a first signal strength in at least one frequency band of the bioelectrical brain signal to a second signal strength in the at least one frequency band of a baseline bioelectrical brain signal.

23. The system of claim 17, wherein the notification comprises at least one of a visible message, an audible signal or a somatosensory notification.

24. The system of claim 17, wherein the one or more processors are configured to determine whether a confidence in the bioelectrical brain signal is greater than or equal to a confidence threshold, and determine the bioelectrical brain signal includes the biomarker in response to determining the confidence in the bioelectrical brain signal is greater than or equal to the confidence threshold.

25. The system of claim 24, wherein the one or more processors are configured to determine whether the confidence in the bioelectrical brain signal is greater than or equal to the confidence threshold by at least comparing at least one of a consistency of the bioelectrical brain signal, a signal strength of the bioelectrical brain signal, or a background noise level of the bioelectrical brain signal to a predetermined threshold value.

26. The system of claim 24, further comprising a medical device including the therapy module, wherein the bioelectrical brain signal comprises a first bioelectrical brain signal and the confidence comprises a first confidence, and wherein the one or more processors are further configured to:
in response to determining the first confidence in the first bioelectrical brain signal is not greater than or equal to the confidence threshold, increment a counter;
after incrementing the counter, determine whether a value of the counter is greater than or equal to a counter threshold;
in response to determining the value of the counter is less than the counter threshold, determine a second confidence in a second bioelectrical brain signal sensed after the first bioelectrical brain signal is greater than or equal to the confidence threshold; and
in response to determining the value of the counter is greater than or equal to the counter threshold, at least one of control the medical device to revert to a safe mode or generate the notification.

27. The system of claim 17, wherein the one or more processors are configured to receive a baseline bioelectrical brain signal, select a signal characteristic of the baseline bioelectrical brain signal, determine a tolerance range for the signal characteristic, and determine the biomarker based on the signal characteristic of the baseline bioelectrical brain signal and the tolerance range.

28. The system of claim 17, wherein the bioelectrical brain signal comprises a first bioelectrical brain signal, the one or more processors being configured to control the therapy delivery by the therapy module based on determining the bioelectrical brain signal includes the biomarker by at least:
prior to generating the notification and in response to determining the first bioelectrical brain signal includes the biomarker, modifying the therapy program to generate a modified therapy program,
controlling the therapy module to deliver therapy to the patient according to the modified therapy program, and
determining a second bioelectrical brain signal sensed after the therapy module delivered the therapy to the patient according to the modified therapy program includes the biomarker,
wherein the one or more processors are configured to generate a notification in response to determining the second bioelectrical brain signal includes the biomarker.

29. The system of claim 28, wherein the one or more processors are configured to modify the therapy delivered by the therapy module by at least modifying at least one therapy parameter value with which the therapy module generates and delivers therapy to the patient.

30. The system of claim 17, further comprising a medical device including the therapy module, wherein the bioelectrical brain signal comprises a first bioelectrical brain signal, and wherein the one or more processors are configured to control the therapy delivery by the therapy module based on determining the bioelectrical brain signal includes the biomarker by at least:
prior to generating the notification and in response to determining the first bioelectrical brain signal includes the biomarker, modifying the therapy program to generate a modified therapy program,
prior to or after modifying the therapy, incrementing a counter that indicates a number of therapy modification attempts,
controlling the therapy module to deliver therapy to the patient according to the modified therapy program,
determining a second bioelectrical brain signal sensed after the therapy module delivered the therapy to the patient according to the modified therapy program includes the biomarker,
determining whether a value of the counter is greater than or equal to a counter threshold,
in response to determining the value of the counter is less than the counter threshold, modifying the modified therapy program, and
in response to determining the value of the counter is greater than or equal to the counter threshold, at least one of controlling the medical device to revert to a safe mode or generating the notification.

31. The system of claim 17, wherein the one or more processors are configured to determine at least one of a number of episodes or a frequency of episodes experienced by the patient, and generate the notification in response to determining the bioelectrical brain signal includes the biomarker and the at least one of the number of episodes or the frequency of episodes experienced by the patient is greater than or equal to an episode threshold.

32. The system of claim 31, further comprising a user interface configured to receive user input indicating an occurrence of an episode, wherein the one or more processors are configured to increment a counter in response to receiving the user input and determine the at least one of the number of episodes or the frequency of episodes based on the counter.

33. A system comprising:
means for delivering therapy to a patient according to a therapy program;
means for storing a biomarker, wherein the biomarker indicates a response of the patient to the therapy delivered by the means for delivering therapy according to the therapy program may have changed relative to a response of the patient to the therapy delivered by the means for delivering therapy according to the therapy program when the patient was in a baseline state in which efficacious therapy delivery by the means for delivering therapy according to the therapy program was observed;
means for receiving information representative of a first bioelectrical brain signal of the patient;
means for determining the first bioelectrical brain signal includes the biomarker; and
means for modifying the therapy program to generate a modified therapy program in response to determining the first bioelectrical brain signal includes the biomarker;

means for controlling the means for delivering therapy to deliver therapy to the patient according to the modified therapy program;

means for determining a second bioelectrical brain signal sensed after the means for delivering therapy delivered the therapy to the patient according to the modified therapy program includes the biomarker; and means for generating a notification in response to determining the second bioelectrical brain signal includes the biomarker.

34. The system of claim 33, further comprising:

means for receiving information representative of a baseline bioelectrical brain signal;

means for selecting a signal characteristic of the baseline bioelectrical brain signal;

means for determining a tolerance range for the signal characteristic; and means for determining the biomarker based on the signal characteristic of the baseline bioelectrical brain signal and the tolerance range.

35. A non-transitory computer readable storage medium comprising instructions that, when executed by one or more processors, cause the one or more processors to:

control a medical device to deliver therapy to a patient according to a therapy program;

select a biomarker stored in a memory, wherein the biomarker indicates a response of the patient to the therapy delivered by the medical device according to the therapy program may have changed relative to a response of the patient to the therapy delivered by the medical device according to the therapy program when the patient was in a baseline state in which efficacious therapy delivery by the medical device according to the therapy program was observed;

receive information representative of a first bioelectrical brain signal of a patient;

determine the first bioelectrical brain signal includes the biomarker;

in response to determining the first bioelectrical brain signal includes the biomarker, modify the therapy program, wherein modifying the therapy generates a modified therapy program;

control the medical device to deliver therapy to the patient according to the modified therapy program;

determine a second bioelectrical brain signal sensed after the medical device delivered the therapy to the patient according to the modified therapy program includes the biomarker; and generate a notification in response to determining the second bioelectrical brain signal includes the biomarker.

* * * * *